United States Patent
Bartol et al.

(10) Patent No.: US 9,084,550 B1
(45) Date of Patent: *Jul. 21, 2015

(54) MINIMALLY INVASIVE NERVE MONITORING DEVICE AND METHOD

(75) Inventors: Stephen Bartol, Windsor (CA); Christopher Wybo, Royal Oak, MI (US)

(73) Assignee: Innovative Surgical Solutions, LLC, Wixom, MI (US)

(*) Notice: Subject to any disclaimer, the term of this patent is extended or adjusted under 35 U.S.C. 154(b) by 925 days.

This patent is subject to a terminal disclaimer.

(21) Appl. No.: 12/605,020

(22) Filed: Oct. 23, 2009

Related U.S. Application Data

(63) Continuation-in-part of application No. 12/040,515, filed on Feb. 29, 2008.

(60) Provisional application No. 61/108,214, filed on Oct. 24, 2008, provisional application No. 61/229,530, filed on Jul. 29, 2009.

(51) Int. Cl.
*A61B 5/06* (2006.01)
*A61B 1/00* (2006.01)
*A61B 5/0488* (2006.01)
*A61B 5/00* (2006.01)
*A61B 5/11* (2006.01)

(52) U.S. Cl.
CPC ............ *A61B 5/0488* (2013.01); *A61B 5/1106* (2013.01); *A61B 5/4029* (2013.01); *A61B 5/4893* (2013.01); *A61B 5/1107* (2013.01); *A61B 5/6828* (2013.01); *A61B 5/7217* (2013.01); *A61B 2505/05* (2013.01); *A61B 2560/0412* (2013.01)

(58) Field of Classification Search
USPC ......... 600/595, 549, 547, 554, 544, 546, 587, 600/373
See application file for complete search history.

(56) References Cited

U.S. PATENT DOCUMENTS

| | | | |
|---|---|---|---|
| 3,200,814 A | | 8/1965 | Taylor et al. |
| 3,565,080 A | | 2/1970 | Ide et al. |
| 4,606,352 A | * | 8/1986 | Geddes et al. ............... 600/515 |
| 4,817,628 A | | 4/1989 | Zealear et al. |
| 5,131,401 A | * | 7/1992 | Westenskow et al. ........ 600/554 |
| 5,284,153 A | | 2/1994 | Raymond et al. |
| 5,284,154 A | | 2/1994 | Raymond et al. |
| 5,425,751 A | * | 6/1995 | Baeten et al. ................... 607/28 |

(Continued)

FOREIGN PATENT DOCUMENTS

| | | | |
|---|---|---|---|
| DE | 19806753 A1 * | 9/1999 | ............ G01D 21/00 |
| WO | 0078209 A2 | 12/2000 | |
| WO | 2007024147 A1 | 3/2007 | |

OTHER PUBLICATIONS

Murphy, Chris; Campbell, Niall; Caufield, Brian; Ward, Tomas and Deegan, Catherine, Micro Electro Mechanical Systems Based Sensor for Mechanomyography, 19th international conference BIOSIGNAL 2008, Brno, Czech Republic.

(Continued)

*Primary Examiner* — Sean Dougherty
(74) *Attorney, Agent, or Firm* — Quinn Law Group, PLLC.

(57) ABSTRACT

A neural monitoring device includes a stimulator configured to provide a stimulus, a mechanical sensor configured to generate an output signal corresponding to a sensed event, and a receiver configured to receive an output signal from the mechanical sensor and determine if the output signal corresponds to the stimulus provided by the stimulator.

26 Claims, 18 Drawing Sheets

(56) References Cited

U.S. PATENT DOCUMENTS

| | | | |
|---|---|---|---|
| 5,775,331 A | 7/1998 | Raymond et al. | |
| 6,324,432 B1 | 11/2001 | Rigaux et al. | |
| 6,466,817 B1 | 10/2002 | Kaula et al. | |
| 6,500,128 B2 | 12/2002 | Marino | |
| 6,564,078 B1 | 5/2003 | Marino et al. | |
| 6,760,616 B2 | 7/2004 | Hoey et al. | |
| 6,807,438 B1 | 10/2004 | Brun Del Re et al. | |
| 6,972,199 B2 | 12/2005 | Lebouitz et al. | |
| 7,050,848 B2 | 5/2006 | Hoey et al. | |
| 7,079,883 B2 | 7/2006 | Marino et al. | |
| 7,177,677 B2 | 2/2007 | Kaula et al. | |
| 7,207,949 B2* | 4/2007 | Miles et al. | 600/554 |
| 7,216,001 B2* | 5/2007 | Hacker et al. | 607/63 |
| 7,236,832 B2* | 6/2007 | Hemmerling et al. | 607/48 |
| 7,470,236 B1* | 12/2008 | Kelleher et al. | 600/554 |
| 7,522,953 B2 | 4/2009 | Kaula et al. | |
| 7,578,819 B2 | 8/2009 | Bleich et al. | |
| 7,582,058 B1 | 9/2009 | Miles et al. | |
| 7,657,308 B2 | 2/2010 | Miles et al. | |
| 7,664,544 B2 | 2/2010 | Miles et al. | |
| 7,668,588 B2 | 2/2010 | Kovacs | |
| 7,691,057 B2 | 4/2010 | Miles et al. | |
| 7,892,173 B2 | 2/2011 | Miles et al. | |
| 7,905,840 B2 | 3/2011 | Pimenta et al. | |
| 7,942,826 B1 | 5/2011 | Scholl et al. | |
| RE42,489 E* | 6/2011 | Chu et al. | 128/898 |
| 7,959,577 B2 | 6/2011 | Schmitz et al. | |
| 7,962,191 B2 | 6/2011 | Marino et al. | |
| 7,991,463 B2 | 8/2011 | Kelleher et al. | |
| 8,000,782 B2 | 8/2011 | Gharib et al. | |
| 8,016,776 B2 | 9/2011 | Bourget et al. | |
| 8,027,716 B2 | 9/2011 | Gharib et al. | |
| 8,055,349 B2 | 11/2011 | Gharib et al. | |
| 8,068,912 B2 | 11/2011 | Kaula et al. | |
| 8,090,436 B2 | 1/2012 | Hoey et al. | |
| 8,133,173 B2 | 3/2012 | Miles et al. | |
| 8,137,284 B2 | 3/2012 | Miles et al. | |
| 8,147,421 B2 | 4/2012 | Farquhar et al. | |
| 8,165,653 B2 | 4/2012 | Marino et al. | |
| 2001/0031916 A1* | 10/2001 | Bennett et al. | 600/383 |
| 2002/0038092 A1 | 3/2002 | Stanaland et al. | |
| 2002/0165590 A1* | 11/2002 | Crowe et al. | 607/48 |
| 2003/0074037 A1* | 4/2003 | Moore et al. | 607/63 |
| 2004/0077969 A1 | 4/2004 | Onda et al. | |
| 2004/0186535 A1 | 9/2004 | Knowlton | |
| 2004/0230138 A1 | 11/2004 | Inoue et al. | |
| 2004/0243018 A1 | 12/2004 | Organ et al. | |
| 2005/0075578 A1* | 4/2005 | Gharib et al. | 600/546 |
| 2005/0085741 A1 | 4/2005 | Hoskonnen et al. | |
| 2005/0102007 A1 | 5/2005 | Ayal et al. | |
| 2005/0113710 A1* | 5/2005 | Stahmann et al. | 600/534 |
| 2005/0115561 A1* | 6/2005 | Stahmann et al. | 128/200.24 |
| 2005/0245839 A1* | 11/2005 | Stivoric et al. | 600/549 |
| 2005/0280531 A1 | 12/2005 | Fadem et al. | |
| 2005/0283204 A1* | 12/2005 | Buhlmann et al. | 607/48 |
| 2006/0020177 A1 | 1/2006 | Seo et al. | |
| 2006/0235484 A1* | 10/2006 | Jaax et al. | 607/46 |
| 2007/0265675 A1 | 11/2007 | Lund et al. | |
| 2007/0276270 A1 | 11/2007 | Tran | |
| 2008/0051643 A1 | 2/2008 | Park et al. | |
| 2008/0125637 A1* | 5/2008 | Geist et al. | 600/372 |
| 2008/0167695 A1* | 7/2008 | Tehrani et al. | 607/42 |
| 2008/0234767 A1 | 9/2008 | Salmon et al. | |
| 2008/0287761 A1 | 11/2008 | Hayter et al. | |
| 2008/0306363 A1 | 12/2008 | Chaiken et al. | |
| 2008/0306397 A1* | 12/2008 | Bonmassar et al. | 600/544 |
| 2008/0312547 A1* | 12/2008 | Wada | 600/534 |
| 2008/0312560 A1 | 12/2008 | Jamsen et al. | |
| 2008/0312709 A1 | 12/2008 | Volpe et al. | |
| 2009/0036747 A1 | 2/2009 | Hayter et al. | |
| 2009/0062696 A1 | 3/2009 | Nathan et al. | |
| 2009/0069709 A1* | 3/2009 | Schmitz et al. | 600/547 |
| 2009/0076336 A1 | 3/2009 | Mazar et al. | |
| 2009/0171381 A1* | 7/2009 | Schmitz et al. | 606/167 |
| 2009/0228068 A1 | 9/2009 | Buhlmann et al. | |
| 2009/0306741 A1 | 12/2009 | Hogle et al. | |
| 2009/0318779 A1 | 12/2009 | Tran | |
| 2010/0137748 A1 | 6/2010 | Sone et al. | |
| 2010/0168559 A1 | 7/2010 | Tegg et al. | |
| 2010/0292617 A1 | 11/2010 | Lei et al. | |
| 2011/0004207 A1* | 1/2011 | Wallace et al. | 606/35 |

OTHER PUBLICATIONS

Koceja, D.M., Bernacki, R. H. and Kamen, G., Methodology for the Quantitative Assessment of Human Crossed-Spinal Reflex Pathways, Medical & Biological Engineeering & Computing, Nov. 1991, pp. 603-606, No. 6, US.

James W. Fee Jr. et al; "EMG Reaction in Muscles About the Knee to Passive Velocity, Acceleration, and Jerk Manipulations"; ScienceDirect Journal of Electromyography and Kinesiology; 2009; pp. 467-475; vol. 19; Wilmington, DE.

M. Tarata et al; "The Accelerometer MMG Measurement Approach, in Monitoring the Muscular Fatigue"; Measurement Science Review; 2001; vol. 1, No. 1.

Bartol, Stephen W., MD, & Laschuk, Maria MD, Arthroscopic Microscopic Discectomy in Awake Patients: The Effectiveness of Local/Neurolept Anaesthetic. Canadian Spine Society Meeting, Vernon, BC, Canada, Mar. 2002.

Bartol, Stephen W., MD, & Laschuk, Maria MD, Use of Nerve Stimulator to Localize the Spinal Nerve Root During Arthroscopic Discectomy Procedures. Canadian Spine Society Meeting, Vernon, BC, Canada, Mar. 2002.

Yoichi Ohta, Norihiro Shima, & Kyonosuke Yabe, Superimposed Mechanomyographic Response at Different Contraction Intensity in Medial Gastrocnemius and Soleus Muscles. International Journal of Sport and Health Science, vol. 5, 63-70, 2007.

* cited by examiner

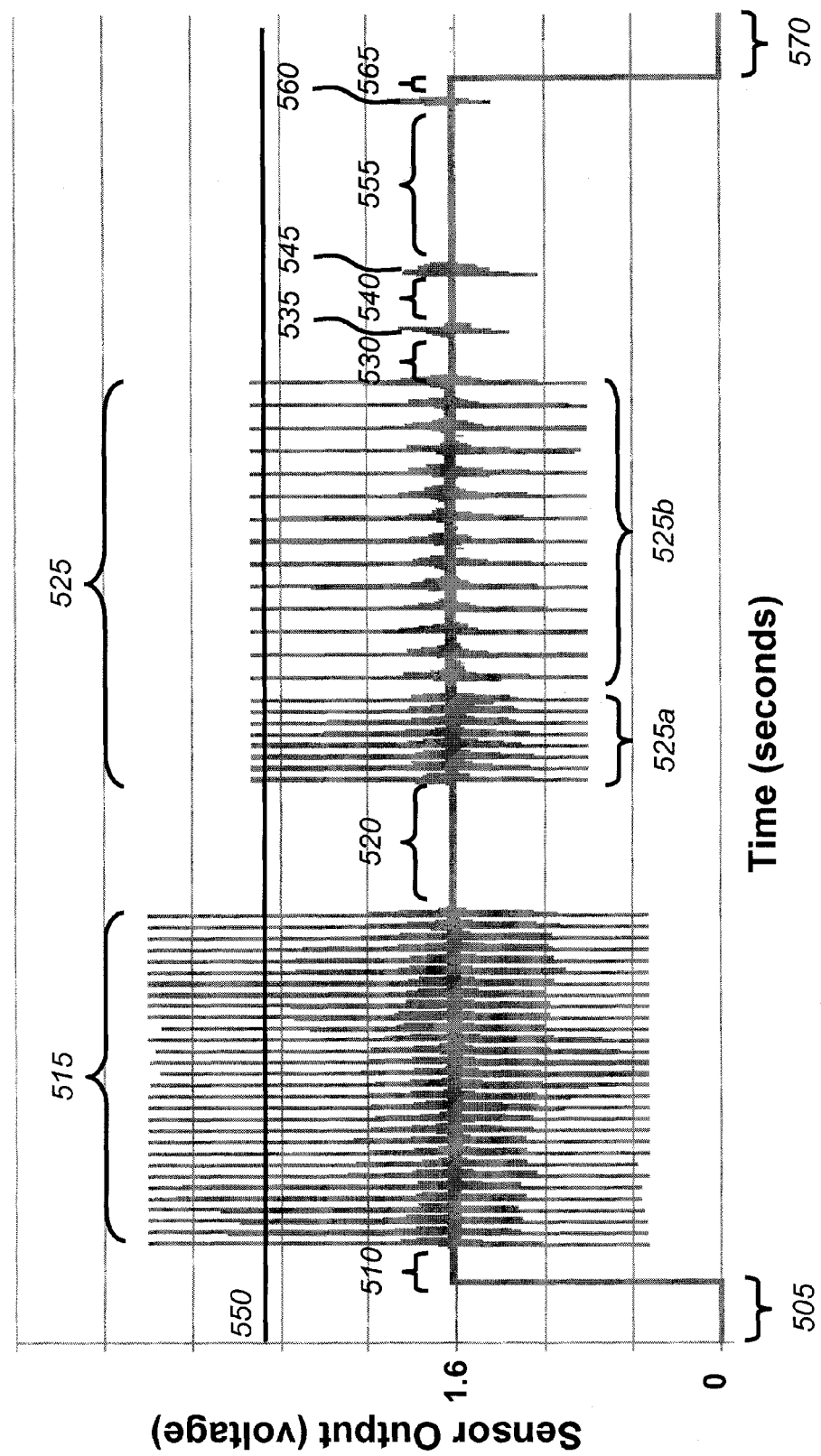

MINIMALLY INVASIVE NERVE MONITORING DEVICE AND METHOD

CROSS REFERENCE TO RELATED APPLICATIONS

This application is a continuation-in-part of and claims the benefit of priority from U.S. application Ser. No. 12/040,515, filed Feb. 29, 2008, which claims the benefit of priority to U.S. Provisional Application No. 60/980,996, filed Oct. 18, 2007, the entire disclosures of which are hereby incorporated by reference as though fully set forth herein. This application additionally claims the benefit of priority from U.S. Provisional Application Nos. 61/108,214, filed Oct. 24, 2008 and 61/229,530, filed Jul. 29, 2009, the entire disclosures of which are hereby incorporated by reference as though fully set forth herein.

BACKGROUND INFORMATION

Nerve injury is a major risk during surgical procedures. Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

Traditionally, the gold standard among nerve location has been direct visualization of a nerve. Direct visualization requires cutting through tissue surrounding the nerve to expose it, thereby allowing a surgeon to look at a nerve to ensure the nerve is not touched or damaged during a procedure.

Another conventional method used is nerve avoidance. By understanding human anatomy, and specifically where nerves should be within the body, a surgeon can work in the areas between the nerves, often referred to as "internervous planes of dissection;' thereby reducing the risk of damaging a nerve during a procedure.

While direct visualization and nerve avoidance can be effective procedures, they may be impractical for certain procedures. For instance, surgery generally involves a significant amount of blood and other fluids that may obscure a surgeon's view. It may be difficult to control fluid flowing in an area of interest, thereby making it difficult to see an exposed nerve, or to determine where adjacent nerves lie. Further, the physical limitations of human anatomy make these procedures impractical for many procedures, That is, the layout of the body is something of an inexact science, and often the location of nerves, much like muscle fibers and even entire organs, can vary between patients. In addition, each of these procedures may require additional operating time, and may necessitate cutting significant amounts of unaffected tissue, resulting in an increase in pain and scarring for a patient, as well as an increased healing time.

A more recent method of nerve monitoring involves electromyography (EMG). EMG is a technique used to measure electrical activity in a motor unit during static or dynamic activity, and to evaluate the health of nerves and corresponding muscles. A motor unit generally can be described as a motor neuron and the associated muscle fibers it innervates, EMG generally includes providing an electrical stimulus to a nerve, or to surrounding tissue, and analyzing an electrical response measured through metal electrodes. EMG requires that the metal electrodes maintain a consistent electrical connection with the innervated area in order to obtain a reading. In one common approach, the metal electrodes are needles which must be driven through the skin, directly into muscle tissue. In another approach, surface electrodes are used. Surface electrodes may require significant preparation of the skin, including first cleaning the skin with alcohol, drying the skin with gauze, then shaving the skin devoid of hair and debriding the skin with pumice stone or sand paper. Once the skin has been properly prepared, EMG surface electrodes must be covered with a conductive gel to improve the electrical connection with the skin. The gel-covered surface electrodes must then be precisely placed to ensure electrical activity within the targeted muscle will be received by the electrodes.

EMG techniques have many drawbacks. EMG requires a complex, time-consuming setup procedure, and often requires a specially trained EMG technician in addition to the surgeon performing the surgery. Not only does this add to the time spent in the operating room, it can significantly increase the cost of surgical procedures. Further, surgeons are often resistant to procedures requiring the services of others. In addition to the complex setup, EMG can be an uncomfortable procedure for the patient. Needle electrodes must be driven through the skin and directly into muscle tissue. The needles may increase the risk of infection, and may lengthen the required healing time after the surgical procedure. Moreover, the needles pose an increased risk for medical professionals, due to the potential for accidental needle sticks. Debridement and skin preparation may be an irritant for patients when surface electrodes are used.

Once the electrodes are in place, it is not uncommon for them to come loose and require reattachment. Needle electrodes may be bumped during a surgery, causing them to be displaced from the target region. Surface electrodes, covered with gel, do not adhere strongly to a patient's skin and thus are prone to falling off. When electrodes lose electrical contact with a target muscle, it may not be apparent to the surgeon or EMG technician. Reattaching electrodes, and interpreting issues associated with electrodes, may further lengthen the time required for a surgical procedure, and may lead to additional frustration. Further, reattachment of electrodes during a surgical procedure may risk contamination of the sterile field. Even when EMG electrodes are properly positioned, electrical signals may be difficult to detect, and difficult to interpret. The EMG electrodes are particularly prone to interference. Accordingly, any electrical device within an operating room may affect electrode outputs. This may require a significant amount of work and interpretation to isolate the portion of readings attributable to EMG. When signals are finally received from electrodes, they are often confusing and difficult to interpret. Resulting signals are often very intricate, including various shapes, sizes, frequencies, etc. Accordingly, interpretation of EMG signals may require significant additional training for a surgeon, or may require the services of a specially trained EMG technician, to obtain meaningful information.

In addition to the foregoing, EMG systems may continually provide stimulation to a target nerve to continually monitor electrical activity. Accordingly, when using EMG systems, the muscles innervated by the targeted nerves may continually fire. This may make it difficult to properly restrain a patient, and make surgery more dangerous. It may also prompt electrodes to come loose.

Further, EMG systems which are turned on intermittently during a surgical procedure generally require a delay while a signal is detected and interpreted. This delay prolongs surgical times, and may create a period of risk and uncertainty.

These and other limitations have led to frustration and a lack of confidence in EMG techniques.

BRIEF SUMMARY

A device, method and system for nerve monitoring are disclosed. The device includes a mechanical sensor such as, but not limited to, an accelerometer, configured to detect a physical response of a muscle or group of muscles in the event that a nerve innervating the muscle or group of muscles responds to a stimulus. The device may also include an indicator which may provide feedback to a user based on at least a portion of an output of the mechanical sensor. The device may be used, for instance, during a surgical procedure to detect proximity to a nerve. In accordance with one exemplary approach, the mechanical sensor includes at least one accelerometer. The accelerometer may be configured to detect muscle motion and/or acceleration.

In accordance with one exemplary approach, a method includes receiving an input from at least one mechanical sensor configured to monitor at least one muscle for a response to a stimulus, and providing a signal representing at least a portion of the input received from the at least one mechanical sensor to a user.

In accordance with one exemplary approach, a system includes a stimulator configured to be positioned within a treatment area. The treatment area may be positioned within a body and may include, or be located near, at least one nerve. The system may also include a mechanical sensor such as, but not limited to, an accelerometer configured to be placed proximate at least one muscle innervated by the at least one nerve. The mechanical sensor may be further configured to monitor the at least one muscle for a response to a stimulus. The system may further include a receiver configured to receive an output from the mechanical sensor, to filter the received output from the mechanical sensor to pass only information indicative of a response to the received stimulus, and to provide an indicator to a user in at least near real time, the indicator indicating whether the at least one muscle is responding to the stimulus.

BRIEF DESCRIPTION OF THE DRAWINGS

FIG. 5 is an exemplary graph of an output from a mechanical sensor.

DETAILED DESCRIPTION

Figure 1:
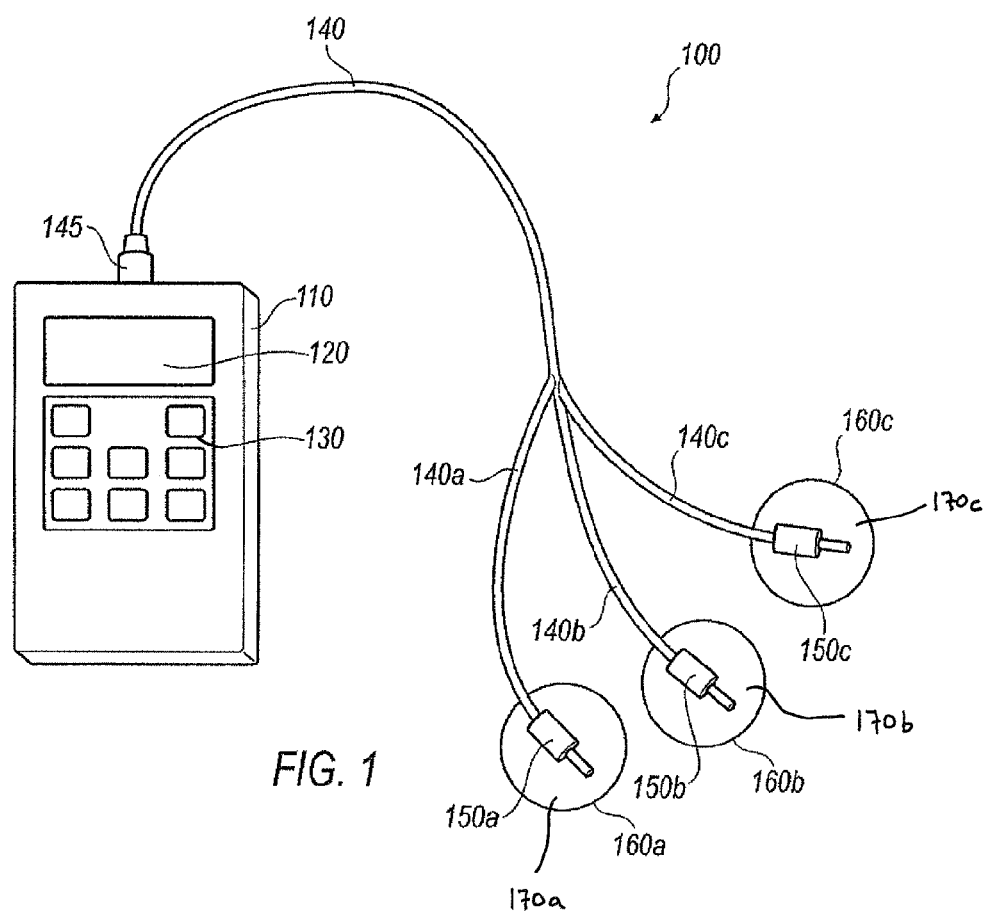
FIG. 1 illustrates an exemplary nerve monitoring device.

FIG. 1 illustrates an exemplary nerve monitoring device 100, including at least one mechanical sensor 160 in communication with a receiver 110 over a connector such as cable 140. In the illustrated approach, receiver 110 includes a display screen 120, and a user interface including a plurality of buttons 130. In one exemplary approach, a receiver, such as receiver 110, may include a touch screen which may provide information to a user and may also act as a user interface capable of receiving input from a user. Receiver 110 may also include one or more icons, light emitting diodes (LEDs), audible indicators, or other devices configured to provide information to a user. The illustrated cable 140 includes a primary connector 150 connected to receiver 110, and a plurality of secondary connectors 155 removably connected to a plurality of mechanical sensors 160.

The receiver 110 may be a stand alone receiver, as illustrated. It is to be understood, however, that this is by way of example, and not of limitation. A receiver 110 may be included as part of another device, including but not limited to a computer, a personal digital assistant (PDA), or other device. Alternatively, receiver 110 may be a device configured to interface with one or more externally connected computers, PDAs, displays, user interfaces, or the like. Receiver 110 may be embodied as hardware, as software, or as a combination of hardware and software. Receiver 110 may be configured to receive outputs from the mechanical sensor 160 and to selectively provide an indicator to a user based on at least a portion of the received outputs. An indicator may be provided through a feedback device that can project a visual and/or audible indicator. Such a feedback device may be used, by way of example and not of limitation, to provide a real-time or near real-time indication of the output received from at least one mechanical sensor 160, or to indicate when the output of at least one mechanical sensor 160 exceeds a predetermined value. A visual indicator may be provided, for example, using a screen, such as screen 120 on receiver 110, on a display incorporated into another device into which receiver 110 is integrated, or a separate display with which receiver 110 may communicate. Audible indicators may be provided, for example, by a speaker (not shown), which may be built in to receiver 110 or provided in another method. Receiver 110 may include one or more user input devices, such as but not limited to, buttons 130, a touch screen, dials, thumb wheels, etc., which may allow a user to interact with the receiver 110. Such user input devices may allow a user to interact with the receiver 110 to, for example, to edit one or more settings within receiver 110.

The mechanical sensor 160 may be configured to be placed proximate a muscle or group of muscles, and to detect a physical action in the muscle or group of muscles. As used herein, a mechanical sensor 160 may be considered proximate a muscle if the mechanical sensor 160 is sufficiently close to the muscle to register a response upon stimulation of the muscle. The physical action may include, for example, muscle motion, acceleration, displacement, vibration, etc. In one exemplary approach, the mechanical sensor 160 may be an accelerometer configured to detect acceleration in at least one axis. Mechanical sensor 160 may be further configured to output a signal in response to the detection of the sensed movement. The output signal may indicate one or more directions, axes, and/or magnitudes, of motion, acceleration, displacement, or vibration experienced by mechanical sensor 160. In an embodiment, mechanical sensor 160 may be accelerometer model MMA7660FC available from Freescale Semiconductor.

The mechanical sensor 160 may be configured to connect directly to the skin of a patient, in an area proximate a muscle or group of muscles. The mechanical sensor 160 may include or be coupled to an adhesive face or patch 170 that allows the mechanical sensor 160 to be quickly and securely adhered to the patient. The mechanical sensor 160 may be configured to be in electrical contact with the muscle or group of muscles, and/or with the skin to which the mechanical sensor 160 is adhered. Alternatively, the mechanical sensor 160 may be electrically isolated from the muscle or group of muscles and/or the skin to which it may be adhered. As used herein, "electrically isolated" includes being generally isolated from the skin of a patient and/or a muscle located beneath the skin. In any event, embodiments indicated as electrically isolated generally do not have sufficient electrical contact with a particular region to provide an EMG signal. In addition, the mechanical sensor 160 may be compatible with a Magnetic Resonance Imaging (MRI) device, thereby allowing a surgeon to employ mechanical sensor 160 in addition to an MRI device during a surgical procedure. The mechanical sensor 160 may include a connector 150 for removably connecting with a cable, such as cable 140. Cable 140 may transmit an output from mechanical sensor 160 to device 110. As used herein, "MRI compatible" includes being constructed of materials that will not significantly affect readings from an MRI device.

The mechanical sensor 160 may be placed proximate a particular muscle or group of muscles to detect whether the muscle exhibits a physical response to a stimulus. Locations for mechanical sensor 160 may be determined based on the particular surgical procedure. A mechanical sensor 160 may be placed quickly, and may be easily repositioned prior to, or during, a surgical procedure. Mechanical sensor 160 does not pierce the skin, and thus may, but need not, be placed within a sterile field. Further, in one exemplary approach, the mechanical sensor 160 does not require a strong electrical connection with the patient. Accordingly, conductive gel need not be placed between the mechanical sensor 160 and the skin. Moreover, the skin need not be thoroughly cleaned, shaved and debrided, as is required with EMG connections. This allows connectors to be attached quickly, and greatly improves reliable adhesion of sensors 160. Furthermore, when a muscle exhibits a physical response to a stimulus, a corresponding response is exhibited not only by the skin directly above the target muscle, but also by the skin in the same general area of the muscle. Thus, whereas EMG electrical sensors must be placed precisely to ensure reliable reading of electrical signals from a target muscle, mechanical sensors 160 need only be placed in the general area of the target muscle. This allows improved reliability, with improved ease of use.

Figure 2:
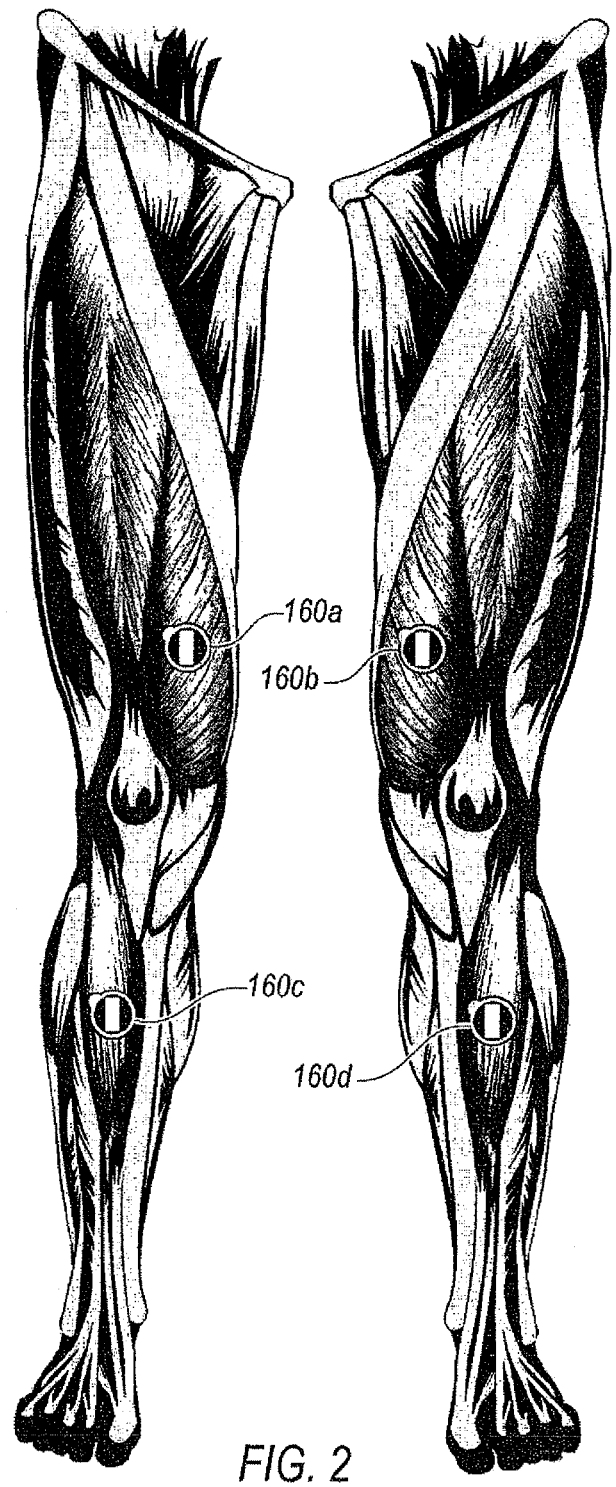
FIG. 2 illustrates a connection of exemplary mechanical sensors to a patient.
Figure 4:
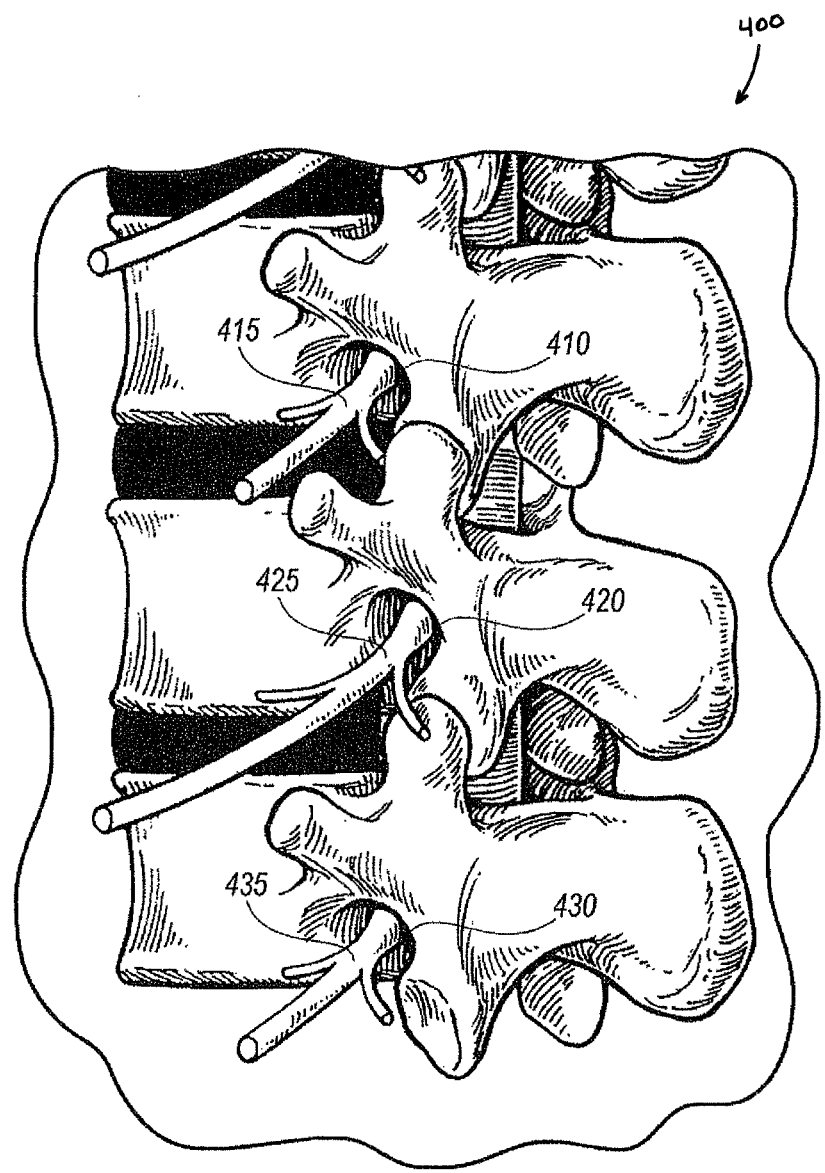
FIG. 4 illustrates a treatment area according to an approach.

Referring now to FIGS. 2 and 4, FIG. 2 illustrates an exemplary placement of a series of sensors 160*a-d* on the legs of a patient. The illustrated sensor placement is meant as an exemplary approach, and is in no way intended to be limiting. FIG. 4 illustrates an exemplary treatment area 400. The illustrated sensor placement may be useful, for example, for monitoring nerves exiting the L2, L3 and L4 foramen (410, 420, 430, respectively,) during a surgical procedure. By way of example, and not of limitation, during a discectomy of the lumbar spine a surgeon may know that the nerves 415, 425 and 435 exiting the L2, L3 and L4 foramen 410, 420, 430 are potentially located in the treatment region 400. The surgeon may then place mechanical sensors 160 on muscles innervated by those nerves 415, 425, 435. For instance, in the illustrated approach, mechanical sensors 160*a* and 160*b* are placed on the vastus medialis muscles, which are innervated by the nerves, such as nerves 415 and 425 exiting the L2 and L3 foramen 410, 420, and sensors 160*c* and 160*d* are placed on the tibialis anterior muscles, which are innervated by the nerves, such as nerve 435, exiting the L4 foramen 430. During the surgical procedure, the surgeon may provide a stimulus within a treatment region, such as treatment region 400. The treatment region may be specific to a particular surgical procedure. For instance, a treatment region may include the area which a surgeon may generally access during a particular surgery. The treatment region may be within the body of a patient (intracorporeal), outside the body, on the surface of the body, such as on the skin of the patient, or any combination thereof. While FIG. 4 illustrates a spinal procedure, it is understood that the present invention may be used in connection with other surgical or therapeutic procedures that are performed in the proximity of motor nerves.

The stimulus provided by the system may be, for example, an electrical charge. In an embodiment, the stimulus may be one or more of a mechanical, thermal, chemical, ultrasonic, infrared, or electrical stimulus. The stimulus may be provided through the insertion of a stimulator, such as stimulator 310 (FIG. 3, described below). Alternatively, a stimulus may be provided by one or more medical instruments typically used for a surgical procedure, such as an endoscope device, a scalpel, etc. A stimulus may be provided constantly during a surgical procedure, or may be selectively delivered by a surgeon. That is, a surgeon may provide a stimulus intermittently during a surgical procedure to a treatment area.

If a nerve is near the provided stimulus, the stimulus will be received by a nerve. Upon receiving the stimulus, the nerve may induce a physical response in the muscles, such as motion, acceleration, displacement, vibration, etc. This muscle response may be registered by one or more mechanical sensors 160. The response may then trigger an output from one or more mechanical sensors 160 which may be transmitted over cable 140 to device 110.

Receiver 110 may provide a response to a user, such as over display screen 120, based on the signal received from the mechanical sensor 160. For example, receiver 110 may provide a graphical representation, such as graph 500 (FIG. 5), or a numerical representation of the output of the mechanical sensor 160, a "Go/No Go" display, or other visual display. A "Go/No Go" style display may, for example, provide a first indication, such as the word "Go," a green light, a "thumbs up," or other indication when the output of the mechanical sensor is within a first range, and may provide a second indication, such as the words "No Go," a red light, a "thumbs down," or other indication when the output of the mechanical sensor is, for example, within a second range, or above a threshold value. Additionally, or alternatively, receiver 110 may be configured to provide an audible alert to a user. An alert may be provided, for example, if the output of the mechanical sensor 160 exceeds a certain value. Alternatively, an audible signal may be provided throughout a procedure and may change based on the received output of the mechanical sensor 160. For instance, an alert may sound with increased regularity, at an increased frequency, at a greater volume, etc., as increased activity is detected by the mechanical sensor 160. A user interface, such as buttons 130, may allow a user to interact with the receiver 110 in order to set values, such as threshold values, and for to format one or more parameters. Parameters may include parameters related to the device, mechanical sensors 160, displays, stimulators, or other elements as may be known.

The receiver 110 may receive an output from the one or more mechanical sensors 160. Receiver 110 may, for instance, compare the received output to a threshold value to determine whether the output exceeds the threshold value. Additionally, or alternatively, receiver 110 may provide the user with a representation of the output of the one or more mechanical sensors 160. In one embodiment, receiver 110 may provide the user with a graphical representation of the output of the one or more mechanical sensors 160, such as graph 500 (FIG. 5).

Figure 3A:
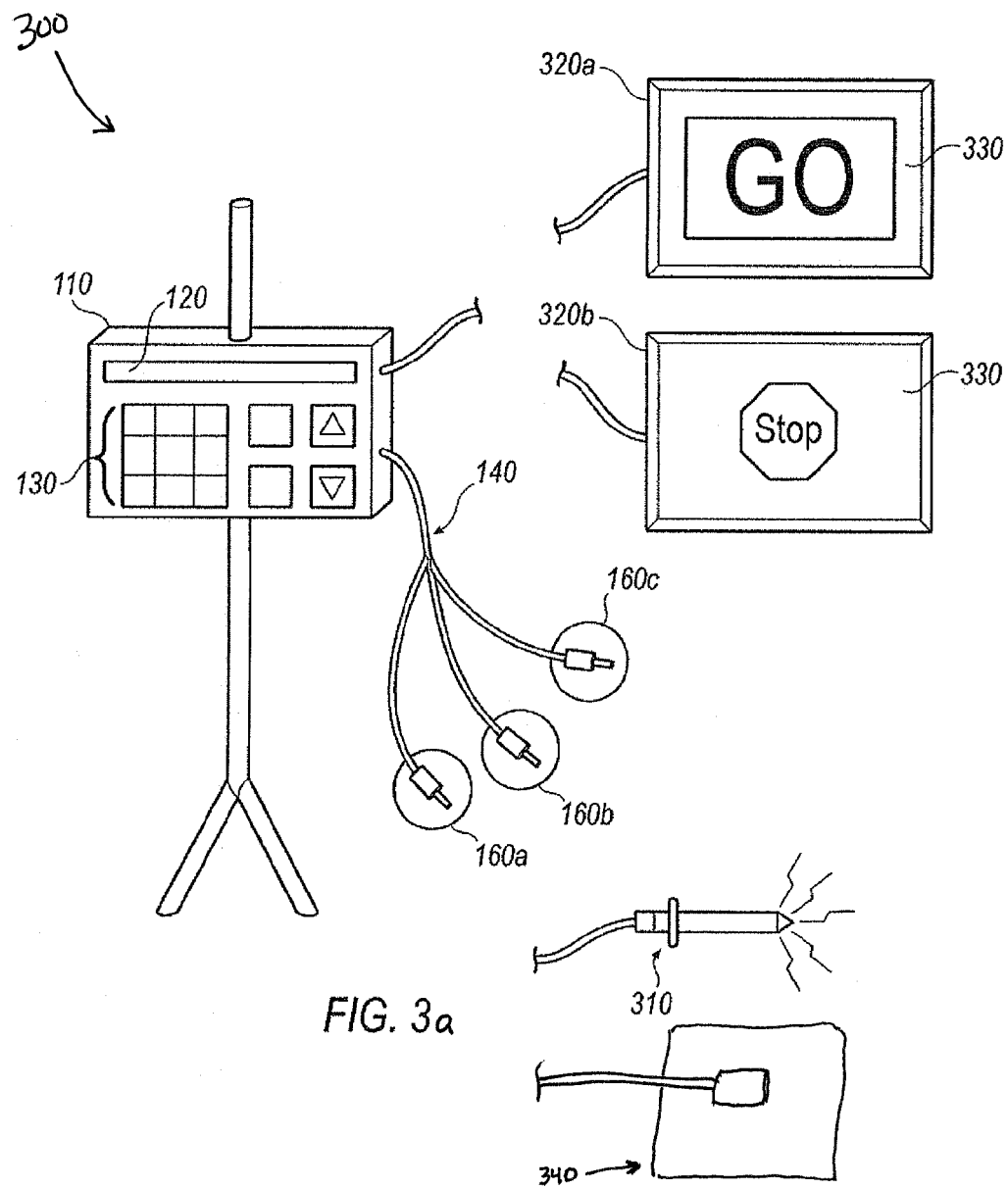
FIG. 3a illustrates an exemplary nerve monitoring system.
Figure 3B:
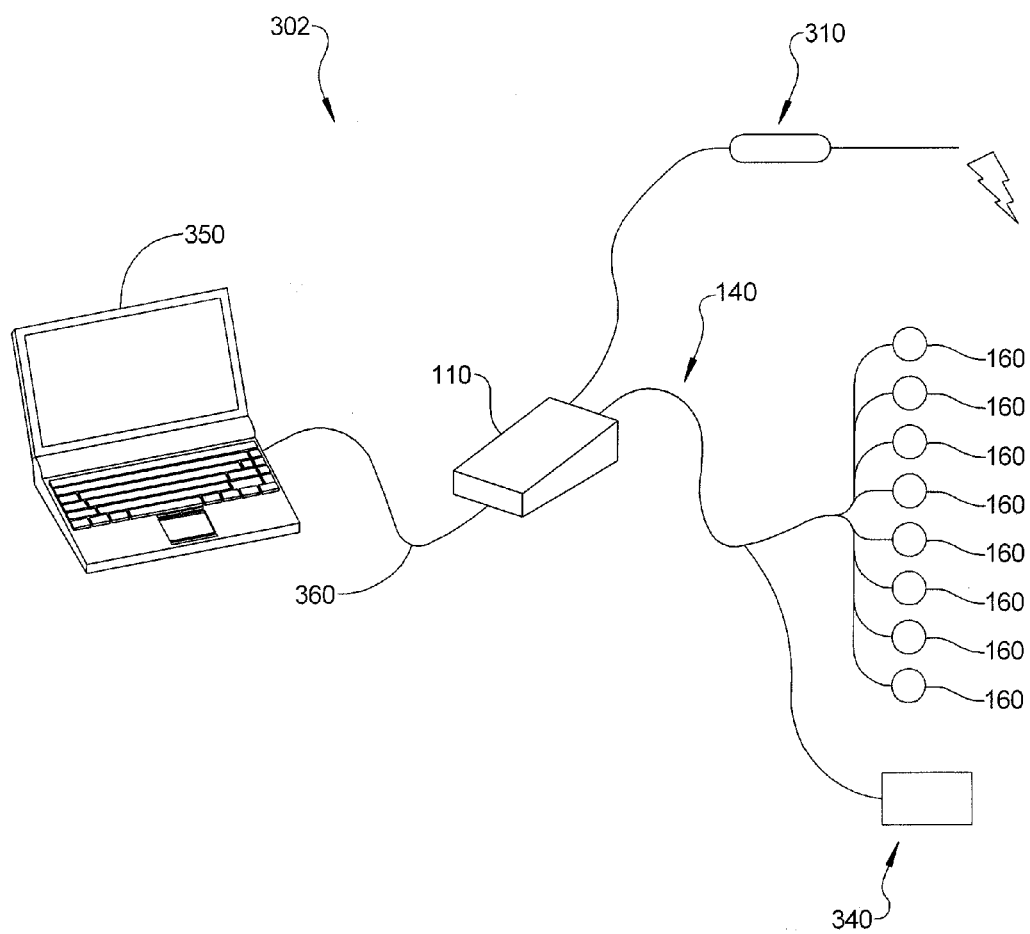
FIG. 3b illustrates an exemplary nerve monitoring system.

FIGS. 3a and 3b illustrate exemplary systems 300, 302 for nerve monitoring. System 300 includes a plurality of mechanical sensors 160 which may communicate with a receiver 110 over a series of cables 140. System 300 includes a stimulator 310, configured to provide a stimulus within a treatment area. Receiver 110 is in communication with a display 320. Display 320 is configured to communicate information related to the output of at least one mechanical sensor 160 using a screen 330. In an exemplary embodiment, as shown in FIG. 3, system 300 may alternate the display 320 between a first state 320a, a second state 320b. Display 320a includes a graphic on screen 330 which may be used to indicate that the output received from mechanical sensors 160 is below a certain threshold value, such as threshold 550 (FIG. 5.) Display 320b includes a graphic on screen 330 which may be used to indicate, for instance, that the output received from at least one mechanical sensor 160 is above a particular threshold value 550 (FIG. 5). System 302, illustrated in FIG. 3b, is similar to system 300, though illustrates an embodiment where receiver 110 is configured to interface with a separate computing device, such as a computer 350 or PDA, via data link 360. In an embodiment, the computing device may have separate data input, display, and/or processing capabilities. In an embodiment, data link 360 may comprise a USB data link. In another embodiment, data link 360 may be a wireless data link, such as a WiFi or Bluetooth data link.

Stimulator 310 may be a stand-alone device, or may alternatively be incorporated into a medical instrument, such as a pedicle probe, needle, guide wire, dilator, retractor, independent multiprobe, elevator, etc. Stimulator 310 may operate independently from receiver 110, or may be in wireless or electrical communication with receiver 110. The stimulator may provide a stimulus, for example, at a point, line, or area on the distal portion of the stimulator. The stimulus may include an electrical signal which may energize, for example, the area around a distal tip of the stimulator. In an embodiment, this area may include the tissue in or around a treatment site, such as treatment site 400 shown in FIG. 4. Alternatively, the stimulus may be a physical stimulus, which may be provided by a stimulator physically contacting a nerve. According to one exemplary approach, a stimulator may provide a constant electrical stimulus throughout a surgical procedure. Alternatively, a stimulator may provide a stimulus intermittently, such as at a regular interval, which may be predetermined, or may be provided selectively, such as upon request by a surgeon. In an embodiment, the stimulator may further include a button configured to be pressed by a surgeon when a stimulus is desired to be applied. During the procedure, a response may be registered by a mechanical sensor 160 positioned on a patient's muscle if the stimulus is provided proximate to a nerve that innervates that same muscle. The surgeon may monitor the output of the one or more mechanical sensors 160 and may thereby determine whether the stimulator delivering the stimulus is located proximate a nerve. A stimulus may be considered proximate a nerve if the stimulus is near enough the nerve to elicit a response in the nerve or innervated muscle.

In an embodiment, an electrical stimulus may include a DC pulse that may be generated at a substantially constant current and a periodic regularity. By "substantially constant," it is understood that with any stepped current, there may be inherent rise times and settling times that may create slight deviations from the desired constant output value. In an embodiment, the amplitude of the current pulse may be variably set in the range of 0-10 mA, and the frequency of the pulse may be variably set in the range of 1-10 Hz. The stimulus may have a 5% duty cycle (i.e. zero volts/amps during 95% of the period), and the pulse width of an exemplary pulse may be 100 us. It should be understood that longer or shorter duty cycles and pulse widths may be used without deviating from the spirit of the invention.

As shown in FIGS. 3a and 3b, system 300, 302 may further include a ground patch 340. In an embodiment, ground patch 340 includes an electrode that is placed in electrical connection with the skin of the patient proximate the treatment site. The electrode may be configured to act as a ground-return for an applied electrical stimulus. Ground patch 340 may further include an adhesive patch that is configured to affix the electrode to the skin of the patient, such as, to the skin of the patient's back. Alternatively, ground patch 340 may be affixed to the skin of the patient using other mechanical means such as straps, bands, or clamps. Ground patch 340 may further be of a sufficient size to allow an adequate disbursement of the electrical stimulus so that the stimulus does not adversely affect any adjoining tissue. In an embodiment ground patch 340 may be, for example, two inches wide, by four inches tall. Ground patch 340 may additionally be configured to be connected to receiver 110 via electrical cabling.

FIG. 5 illustrates an exemplary output of a mechanical sensor 160 during a procedure, where mechanical sensor 160 is an accelerometer. Graph 500 represents the output of a first accelerometer 160 over a period of time, encompassing a number of distinct regions. In the first region, 505, the mechanical sensor 160 is powered off and has zero output. In the second region 510 the mechanical sensor 160 has been placed on the patient and has been powered on, though at this time, the nerve or nerves innervating the target muscle or muscle group have not been stimulated. As shown, zero sensed motion may correspond to a nominal voltage offset above zero volts. The transition from zero volts to such a nominal voltage may indicate to the system that the patch is connected and that it is safe to proceed or continue with a procedure. In the third region, 515, a stimulus has been provided near the target nerve. The stimulus provided during this third region 515 may be sufficiently large and/or sufficiently near a nerve that the stimulus elicits a response in the nerve. The exemplary stimulus provided during the third region 515 is an electrical signal having a frequency of approximately 2 Hz, although it is to be understood that other stimuli may be used. A corresponding response is registered by the mechanical sensor 160, the output of which is displayed on graph 500. The illustrated response has a frequency similar to the frequency of the provided stimulus. The magnitude of the illustrated response of the third region 515 is greater than the threshold value 550. In the illustrative example, a particular threshold value 550 was selected, though it is to be understood that other magnitudes may be selected, as desired. In the fourth region, 520, the stimulus is no longer being registered by the nerve and accordingly, the output from the accelerometer 160 returns to near its normal, nominal output voltage. This may signify to a surgeon that it is again safe to continue with a medical procedure. In the fifth region, 525, the stimulus is again received by a nerve, causing a corresponding physical response near the target region. The stimulus provided during the fifth region is altered from a 2 Hz electrical signal (525*a*) to a 1 Hz electrical signal (525*b*), causing a corresponding change in the reaction of the innervated muscle and a mechanical sensor 160 connected thereto. While the response registered by mechanical sensor 160 in region 525*a* has a frequency greater than the response registered in region 525*b*, the magnitude of the registered response still exceeds the threshold value 550. The stimulus is again removed in the sixth, eighth, tenth and twelfth regions, 530, 540, 555, and 565, respectively. The seventh, ninth, and eleventh regions, 535, 545 and 560, illustrate an exemplary response registered by the mechanical sensor 160 to a stimulus other than the excitation of a nerve. For example, in the exemplary regions 535, 545 and 560, the operating table may have been bumped by the surgeon. Finally, in region 570, the mechanical sensor 160 is again powered off, and returns to zero output.

As illustrated in graph 500, the response registered by a mechanical sensor 160 to a stimulus provided to a nerve may be significantly greater than the response registered from another stimulus (e.g. 535, 545, 560). Accordingly, a "Go/No Go" style display may display "No Go" when a response registered by a mechanical sensor 160 is above threshold 550, such as during regions 515 and 525, and may display "Go" when a response is not registered from a mechanical sensor 160, or when a response registered by a mechanical sensor 160 is below threshold 550, such as during regions 510, 520, 530, and thereafter.

While graph 500 illustrates the output of a single mechanical sensor 160, it is to be understood that this is by way of example and not of limitation, and a graph 500 may additionally include representations of the output of multiple mechanical sensors 160. Moreover, as shown in FIGS. 6*a*-6*d*, a display such as display 120, may independently illustrate the output of one or more mechanical sensors 160, one or more 'Go/No Go" signals related to one or more mechanical sensors 160, as well as other information relevant to the procedure.

FIGS. 6*a*-6*d* illustrate exemplary display screens 600 which may be presented to a user on display 320. A user may interact with the display screen 600. For instance, display screen 600 may be a touch screen. Alternatively, a user may interact with screen 600 using an input device such as a computer mouse. The display screens 600 may include a sensor overview region 610 including status indicators 620*a*-620*h*. In the exemplary approach, each of the status indicators 620 is labeled according to a corresponding to a muscle. The status indicators 620 are each associated with a respective mechanical sensor 160 which is placed on or near the muscle corresponding to the label on the status indicator 620. The status indicators include visual representations of the status of each sensor, such as a GO/NOGO indicator, a check mark, a green circle, etc., if the mechanical sensor 160 associated therewith is connected to a patient, and is not registering motion. The display screens 600 may also include an overall status indicator 630. The overall status indicator 630 may represent a first value, such as "GO" (FIG. 6*a*) when all of the individual status indicators 620*a*-620*h* indicate all of the associated mechanical sensors 160 are connected to the patient, and do not register motion.

Figure 6A:
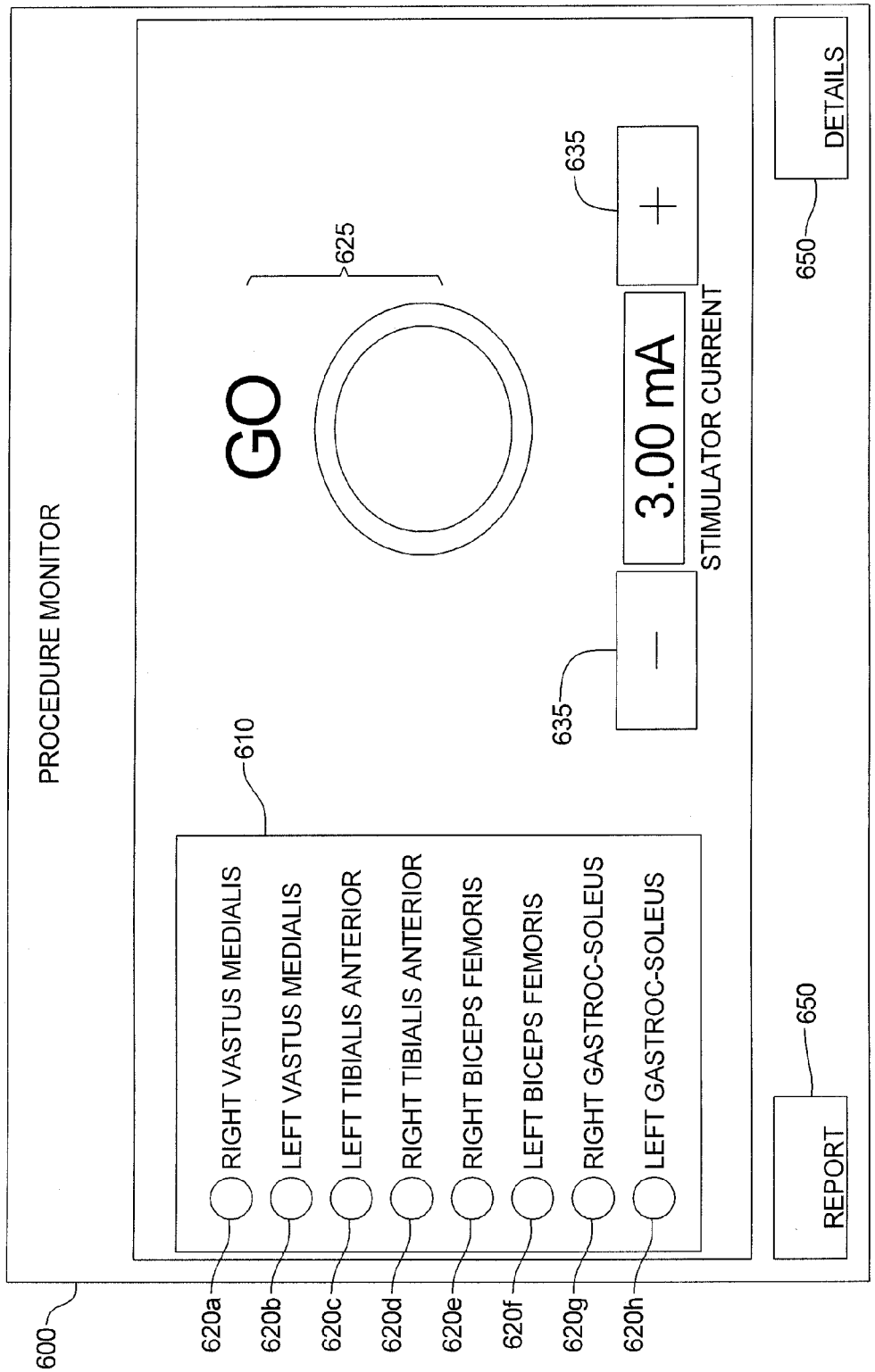
FIGS. 6a-6d illustrate exemplary nerve monitoring system display screens that may be conveyed to a user.
Figure 6B:
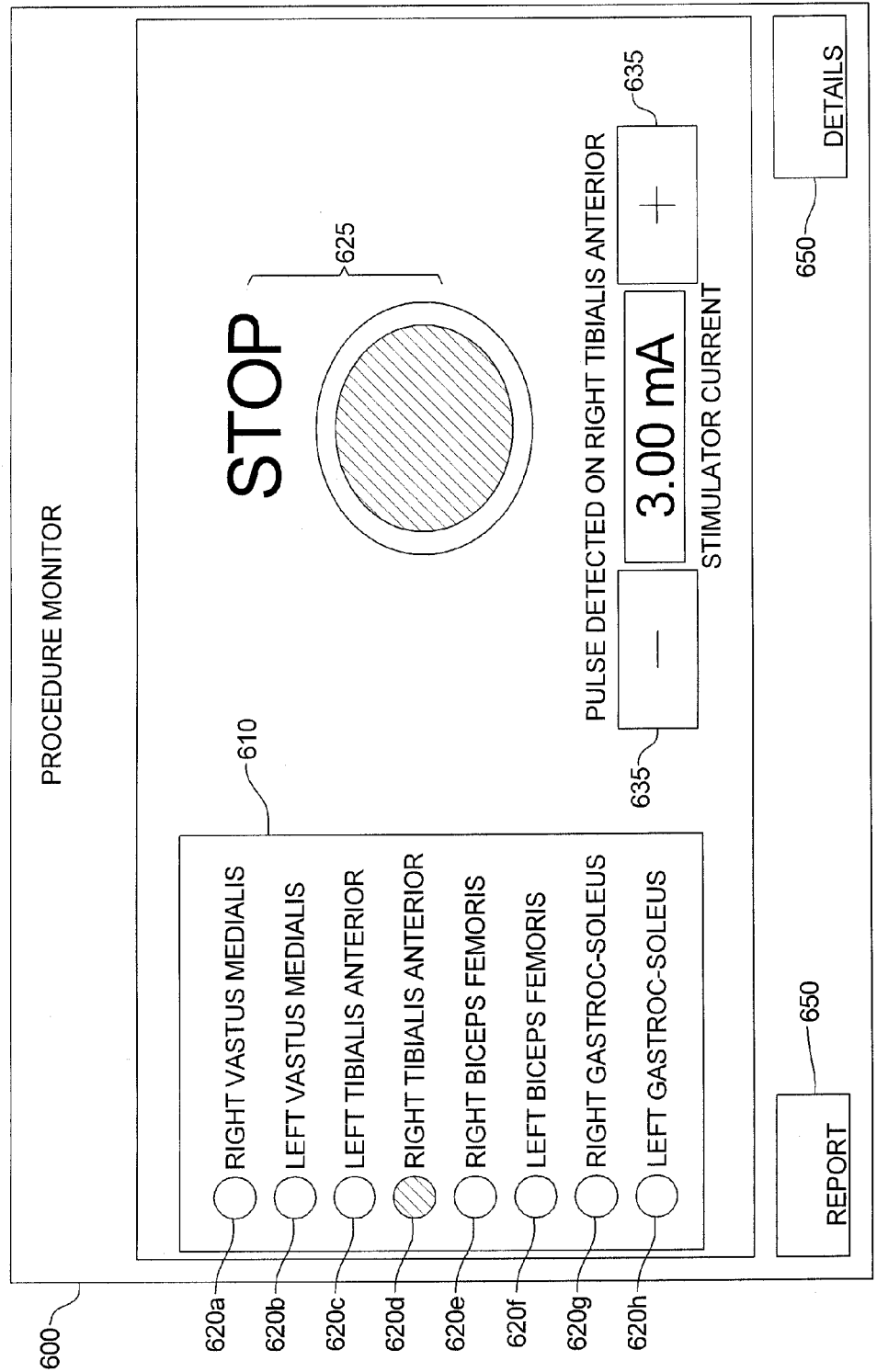

If any of the mechanical sensors 160 become detached from the patient, or the mechanical sensors 160 detect muscle movement, the status indicator 620 associated with the mechanical sensor 160 may change to another value, such as "NOGO", a Stop Sign, an "X", a red circle, etc. (see FIG. 6*b*). As illustrated in FIG. 6*b*, if any of the individual status indicators 620 become detached or register motion, the overall status indicator 630 may change from "GO" to another value such as "STOP". A corresponding graphic may also change, such as by changing shape or changing from a first color, such as green, to a second color, such as red.

Display screen 600 may also include other information, such as the value of the current provided by the stimulator 310. A user may be able to adjust the value, such as by using buttons 635 or a selector on stimulator 310. The user may also be provided with additional options, such as the ability to view additional information by choosing one or more icons 650.

Figure 6C:
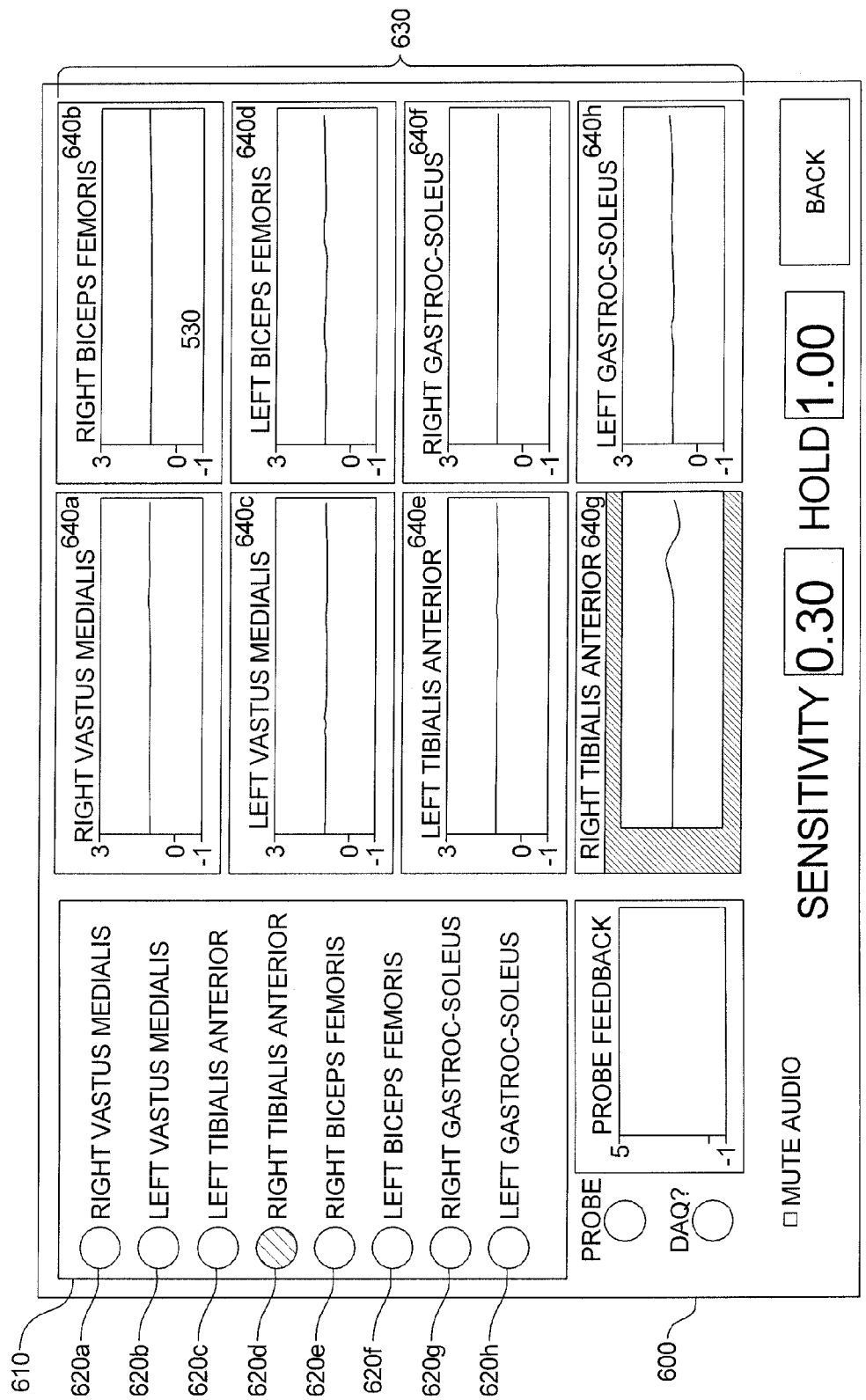

FIG. 6*c* illustrates an exemplary display screen 600 including a sensor overview region 610. The sensor overview region 610 includes individual status indicators 620*a*-620*h* for each of a plurality of mechanical sensors 160. Each of the status indictors 620 are labeled according to the muscle which the associated mechanical sensor 160 is placed on or near. The display screen 600 also includes a graph region 630 which includes individual graphs 640*a*-640*h* representing the actual output of each mechanical sensor 160 associated with each of the muscles listed in the sensor region 610. The graphs 640*a*-640*h* may provide real-time or near-real-time indications of the output of each of the mechanical sensors 160 used during a surgical procedure.

Figure 6D:
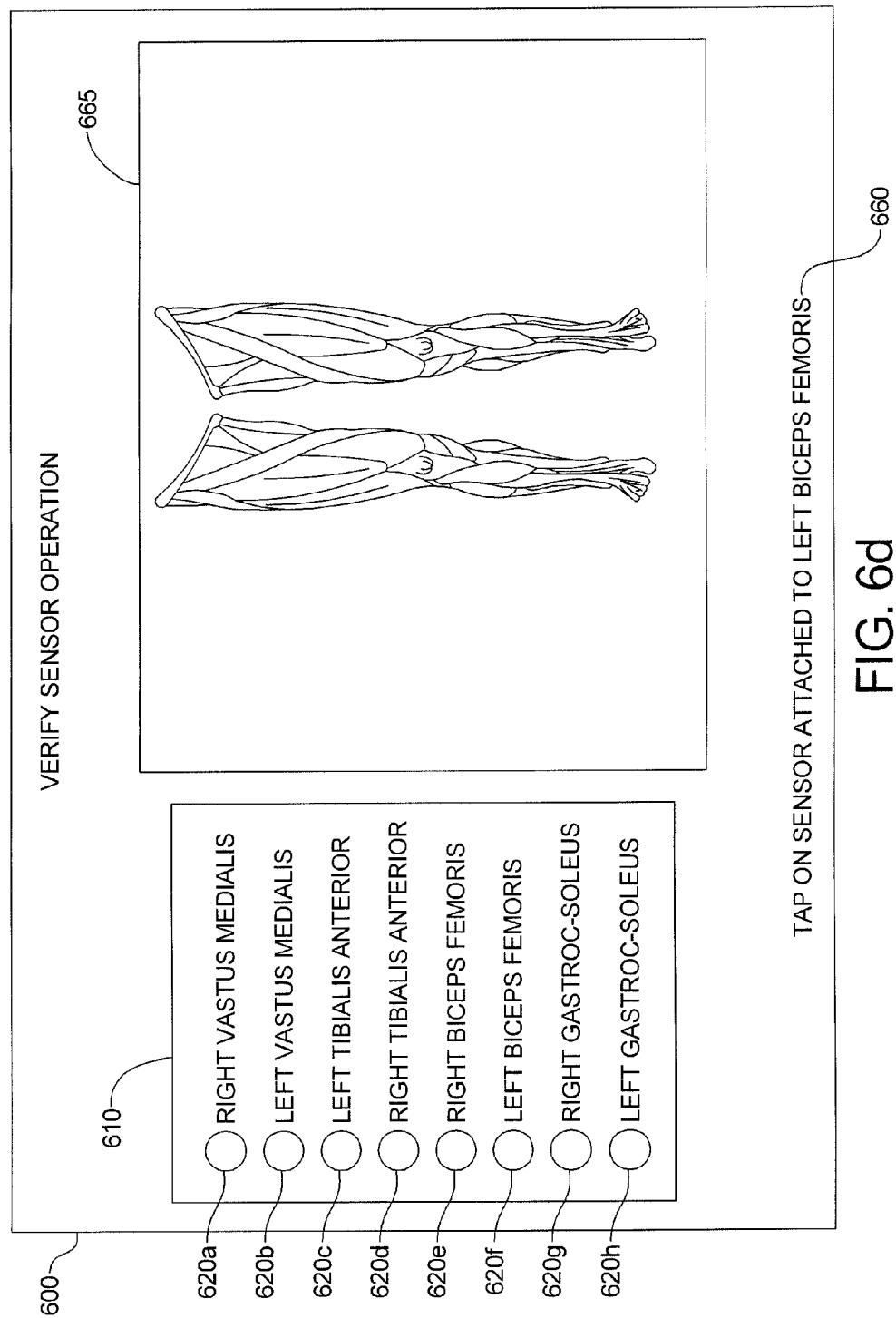

FIG. 6*d* illustrates an exemplary display screen 600 for use during the setup phase of a procedure. The display screen 600 may be configured to direct a surgeon or technician in the proper positioning of sensors. In one approach, a display screen 600 may include graphics 665 and prompts 660 indicating areas on a patient to place a mechanical sensor 160. A sensor status indicator 620 may be represented by a particular graphic or value, such as a yellow circle, when the system is in a setup mode. The system may then direct the user to place a mechanical sensor 160 associated with a sensor status indicator 620 on a particular muscle. The output of the mechanical sensor 160 may be monitored, to determine when the sensor 160 is placed. After the sensor is placed, and functioning, the sensor status indicator 620 may be updated with a subsequent graphic or value, such as a green circle, a check mark, etc. By instructing the user on where to place each mechanical sensor 160, the system may be assured that indicators associated with each of the listed muscles are properly monitored.

In an exemplary procedure, a surgeon may identify a first treatment region in which to begin a surgical procedure. Throughout the surgical procedure the surgeon may stimulate the area in which the surgeon is working, while monitoring the output of at least one mechanical sensor 160. If at any point there is a response registered by a mechanical sensor 160, the surgeon may temporarily pause the procedure. The surgeon may determine, based on the registered response, whether it is safe to continue the procedure in the present location. The surgeon may determine whether it is safe by, for instance, viewing the magnitude of the registered response, or based on whether the response is a "Go" or a "No Go" response. If the surgeon determines that it is not safe to continue in the present location, the surgeon may determine another location at which to continue the procedure. For instance, the surgeon may approach an area from a different angle, using a different treatment method, or otherwise alter the surgery. The surgeon may determine the safety of a subsequent method or approach by stimulating the proposed area, and monitoring a mechanical sensor 160. Additionally or alternatively, a surgeon may stimulate one or more areas within, or near, a proposed treatment region in an effort to identify or locate nerves prior to, or during, a surgical procedure.

Although exemplary embodiments of the mechanical sensor 160 have generally included an accelerometer, it is to be understood that this is by way of example and not of limitation. A mechanical sensor may include other types of mechanical sensors, or motion sensors, as desired. Additionally, a mechanical sensor 160 may include more than one sensor, which may, but need not, be the same type of sensor.

Figure 7:
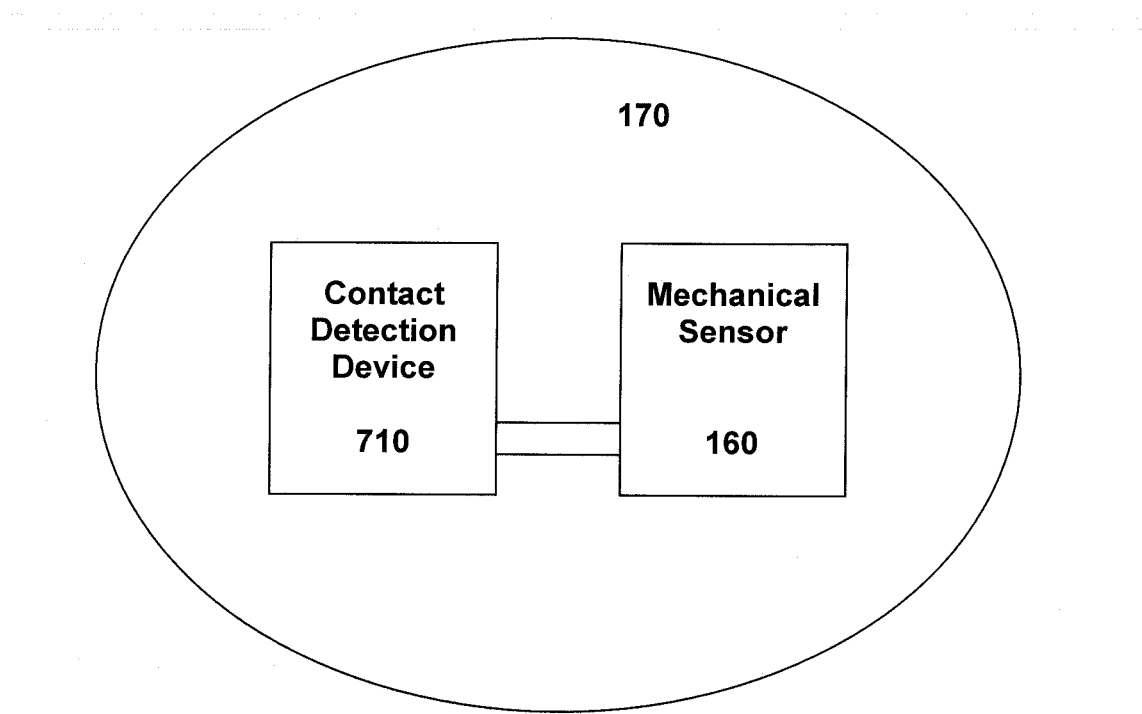
FIG. 7 is an exemplary sensor including a contact detection device.

As generally shown in FIG. 7, in an embodiment, one or more of the mechanical sensors 160 or the ground patch 340 may include, or be coupled with, a contact detection device 710 configured to detect whether the respective sensor or patch is in physical contact with the patient. In an embodiment, the contact detection device may be integrated into the adhesive face 170 of the sensor. The contact detection device 710 may comprise, for example, a physical switch or button, a capacitive switch, a field effect switch, a photodiode, or other comparable means of presence detection. In an embodiment, the contact detection device 710 may energize the mechanical sensor 160 only when it detects that the sensor is in physical contact with the patient.

In an embodiment, the contact detection device may be configured to provide the receiver 110 with an indication of whether the corresponding mechanical sensor 160 or ground patch 340 is in physical contact with the patient. Such an indication may comprise a signal transmitted to the receiver 110 to indicate contact or non-contact, or may comprise an interruption in the data output from the mechanical sensor (e.g. FIG. 5, sections 505 and 570). In an embodiment, the contact detection device may interrupt the data output from the mechanical sensor 160 by selectively powering the mechanical sensor 160 only when the device comes in contact with the patient. In this approach, the contact detection device may be connected in series with sensor, and only power the sensor when contact is detected. This indication may be used by the system to determine whether the sensor output bears a relationship to the applied stimulus, as generally described above with respect to FIG. 5. If the mechanical sensor 160 becomes detached from the patient, the receiver 110 may alert the physician through either a visual or audible alarm. Such an alarm may prevent the physician from maintaining a false sense of security when the mechanical sensor 130 is registering no muscle response solely because it has become detached from the patient. Such a false sense of security may, for example, exist if the system were indicating a safe or GO status despite the existence of unsafe, though undetected, muscle response to the stimulus.

Figure 8:
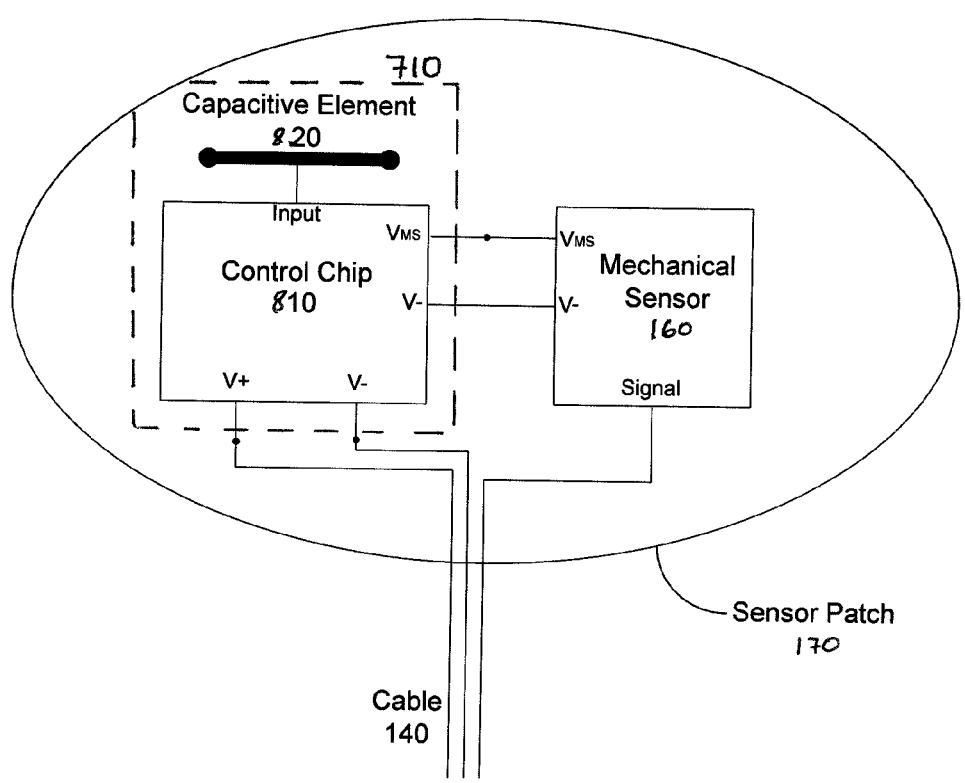
FIG. 8 illustrates an exemplary sensor including a capacitive switch contact detection device.

FIG. 8 illustrates an exemplary embodiment of the contact detection device 710, comprising a capacitive switch. In such an embodiment, a control chip 810 may be coupled to a capacitive element 820 and a mechanical sensor 160. The capacitive element 820 may be, for example, an electrode. The mechanical sensor 160 may be, for example, an accelerometer. The control chip 810 may be a capacitive switch. In one exemplary approach, the control chip may be a Quantum™ Research Group QTouch™ Chip, available through Atmel Corporation of Westlake Village, Calif., USA.

The control chip 810 may be configured to charge the capacitive element 820 to about a known electrical potential. After the capacitive element 820 has been charged to about this known electrical potential, the capacitive element 820 may output a charge to the control chip 810. The control chip may use the electrical potential and the output received from the capacitive element to determine the capacitance of the capacitive element, using the formula Capacitance=Electrical Charge divided by Electrical Potential (C=Q/V). The control chip 810 may be further configured to recharge the capacitive element 820 to about the known electrical potential, and to again receive an electrical charge output thereby. The control chip 810 may continually charge the capacitive element 820 and receive subsequent outputs, thereby continually monitoring the electrical charge output by the capacitive element 820. The control chip 810 may also monitor the capacitance of the capacitive element 820. By monitoring the charge on the capacitive element 820, and/or by monitoring the capacitance of the capacitive element 820, the control chip may detect when the charge and/or capacitance changes. A change in the capacitance may indicate that the mechanical sensor 160 has been placed proximate, or removed from, a patient.

As described above, in an embodiment, the control chip 810 may selectively power the mechanical sensor 160. For instance, the control chip 810 may be configured such that the mechanical sensor 160 is only powered when the capacitive element has a particular capacitance, or outputs a particular charge (i.e. when the contact detection device senses contact). The control chip 810 may thus power the mechanical sensor 160 only when the sensor patch 170 is connected to a patient. The mechanical sensor 160 is coupled to the control chip 810 to receive power therefrom. The mechanical sensor 160 is also configured to provide an output signal when powered. The output signal may be a generally constant value when the mechanical sensor 160 does not detect mechanical motion, and may be another value when the mechanical sensor 160 detects mechanical motion. For instance, the output of the mechanical sensor 160 may spike when the sensor 160 detects motion. When the sensor is not powered, the sensor 160 generally does not output a signal.

In another embodiment, contact detection device 710 may include a field effect switch. Such a detection device may operate by generating an electromagnetic field between adjacent polarized electrodes and then by measuring perturbations of the field due to outside influences such as the physical proximity of a patient's skin. One such field-effect switch may be the TS100 TouchCell, commercially available from TouchSensor Technologies, LLC.

During operation, the system may be configured to only provide a safe or "GO" signal if all mechanical sensors 160 are attached to the patient, the ground patch 340 is electrically coupled with the patient, and no muscle response is detected. If the system detects that a mechanical sensor 160 or ground patch 340 has lost contact with the patient, the system may be configured to alert the physician through an audible alert, or a visual alert such as a stop sign or "NO GO" warning. This warning may be used to convey that the nerve monitoring system is non-operational, and may be combined with additional indicators to identify the disconnected device to the physician. As described above, the system may also be configured to alert the physician if the entire system is operational and connected and a muscle response exceeds a threshold.

Therefore, a "GO" signal may represent a fully functioning system where a nerve is not proximate to the stimulator, while appropriate alternate warnings may further indicate that either the system is either non-operational and must be reconnected, or that a nerve is in proximity to the stimulator.

Figure 9:
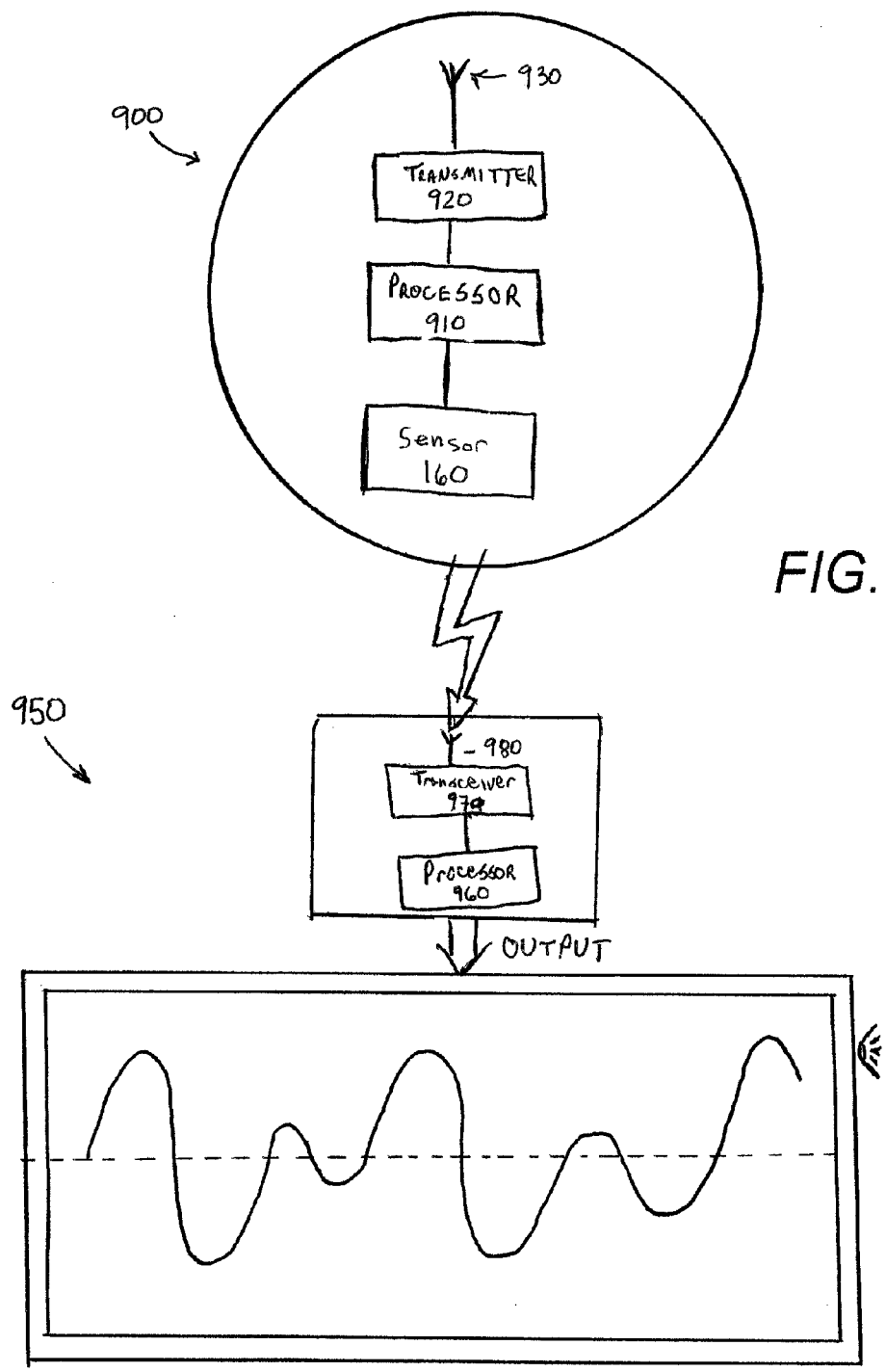
FIG. 9 illustrates an exemplary wireless nerve monitoring system including a remote workstation.

In an embodiment, one or more mechanical sensors 160 may include the ability to transmit data wirelessly to receiver 110, either independently, or collectively. FIG. 9 illustrates an exemplary wireless sensor 900 and receiver 950, configured to accept wireless signals. Wireless sensor 900 includes a mechanical sensor 160, a processor 910 in communication with a mechanical sensor 160, a transmitter 920 in communication with the processor 910, and an antenna 930 coupled with the transmitter 920. Wireless sensor 900 may further include an adhesive face or patch 170 configured to adhere the mechanical sensor 160, processor 910, transmitter 920, and antenna 930 to the skin of a patient.

Processor 910 may be a microcontroller configured to receive and process output signals from mechanical sensor 160. Processor 910 may be configured to prepare and output data packets. Data packets may include data representative of at least a subset of the accelerometer output. Data packets may further include identifier information which may identify the processor 910, the mechanical sensor 160, the wireless sensor 900, etc. Processor 910 may provide data packets to transmitter 920 for transmission. In an embodiment, processor 910 may be microcontroller model MC9S08QG8 available from Freescale Semiconductor.

Transmitter 920 may be configured to receive data packets from processor 910 and to transmit the data packets to an associated receiver. Packets may be transmitted according to a wireless protocol, and/or at an appropriate frequency. Transmitter 920 may be a transceiver, capable of two way communication with one or more remote devices, such as a remote transceiver. Transmitter 920 may transmit the data packets as they are received from processor 910, in real time, or near-real time. Alternatively, transmitter 920 may send burst of data incorporating a number of data packets into a single transmission. Transmitter may be coupled to antenna 930. In an embodiment, transmitter 920 may be transmitter model number MC33696 from Freescale Semiconductor.

One of skill in the art will recognize that wireless sensor 900 may include other elements, such as a battery, memory, and/or other circuitry, though these elements are omitted from FIG. 9 for the sake of clarity.

As illustrated in FIG. 9, an exemplary wireless receiver 950 is configured to receive outputs from wireless sensor 900. Wireless receiver 950 may be similar in function and operation as receiver 110, but may further include the ability to receive the output from one or more wireless sensors 900. In an embodiment, wireless receiver 950 may include a processor 960, a transceiver 970 coupled to the processor 960, and an antenna 980 and configured to receive signals transmitted by an associated device, such as wireless sensor 900. Transceiver 970 may provide the received signals to the processor 960. Processor 960 may parse received signals to determine, for example, sensed mechanical data such as acceleration, sensor identifiers, etc. The parsed information may then be provided to a user using an output device, such as an attached monitor 990, a speaker 995, etc.

Figure 10:
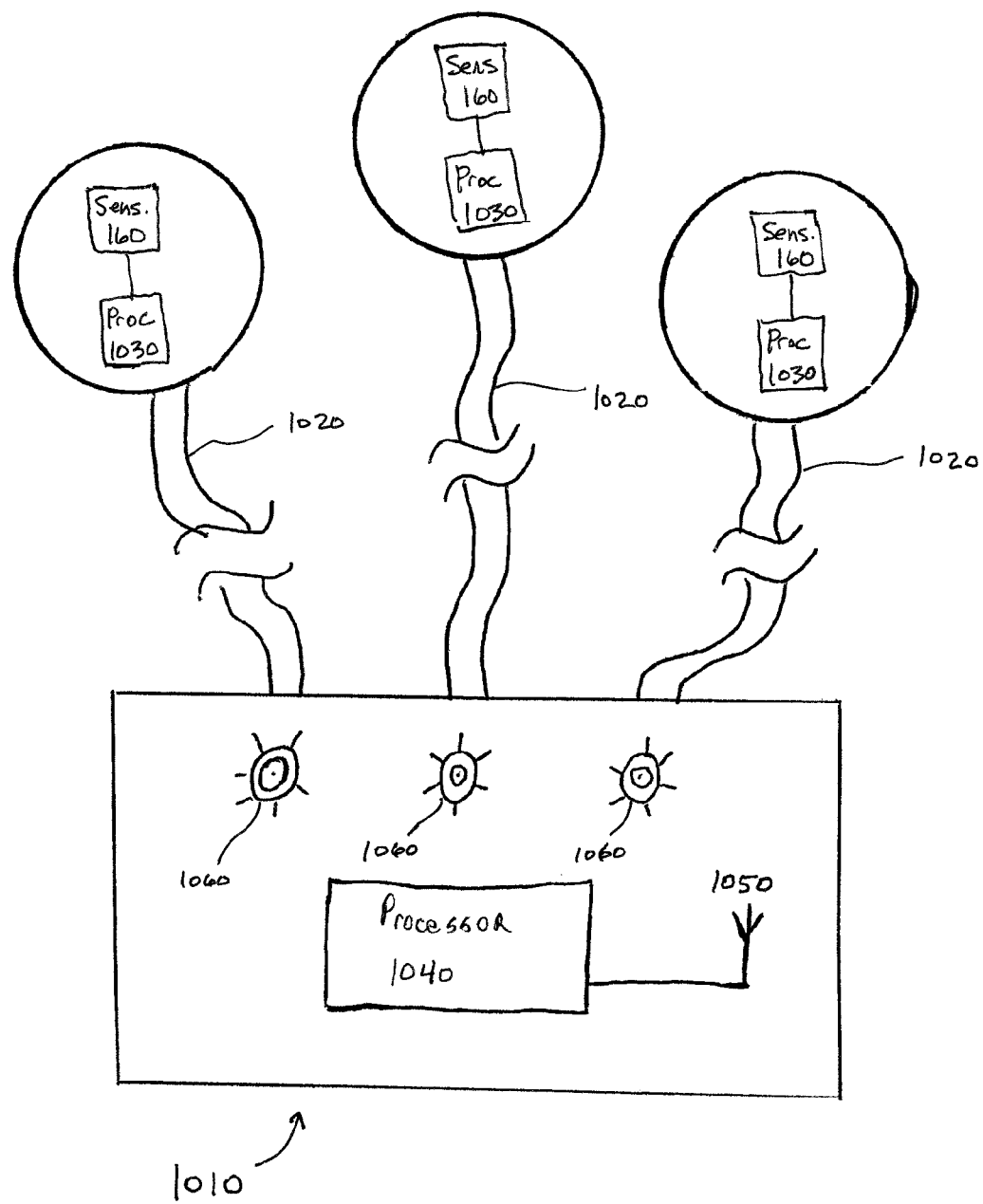
FIG. 10 illustrates an exemplary wireless nerve monitoring system including a common transmitter.

FIG. 10 illustrates an exemplary mechanical sensor configuration and wireless receiver 950 according to another exemplary embodiment. The system includes one or more mechanical sensors 160 coupled with a common transceiver 1010. Mechanical sensors 160 may be coupled to transceiver 1010 through respective wires 1020. In an embodiment, each mechanical sensor 160 may include a local processor 1030. Each mechanical sensor 160 may further include memory (not shown) which may contain information regarding the sensor, such as an identifier uniquely identifying the associated sensor, and/or temporary sensor data. Each mechanical sensor 160 may be configured to provide a signal to the common transceiver 1010 indicative of the sensed parameters. Transceiver 1010 may include a processor 1040 and may be configured to receive signals from one or more of the mechanical sensors 160 and to transmit signals to a wireless receiver 950 similar in function to receiver 110.

Transceiver 1010 may include an antenna 1050 configured to transmit sensors. In an embodiment, transceiver may further include one or more indicators 1060. Transceiver 1010 may include an indicator 1060, such as a light, for each associated mechanical sensor 160. Indicators may be configured to indicate the status of an associated mechanical sensor 160. While the illustrated approach includes mechanical sensor 160 coupled to common transceiver 1010 via wires 1020, it is understood this is by way of example only, and not of limitation. Mechanical sensors 160 may additionally communicate with the common transceiver 1010 using a wireless protocol such as, but not limited to, Bluetooth wireless protocol. Transceiver 1010 may be located proximate the patient, and may transmit associated sensor signals to a wireless receiver 950 using a wireless protocol which may be, but need not be, the same protocol by which mechanical sensors 160 communicate with transceiver 1010. Transceiver 1010 may be configured to transmit at a higher power level than the level at which mechanical sensors 160 transmit, thus allowing sensors to operate at a lower power level, which may preserve battery life.

Figure 11:
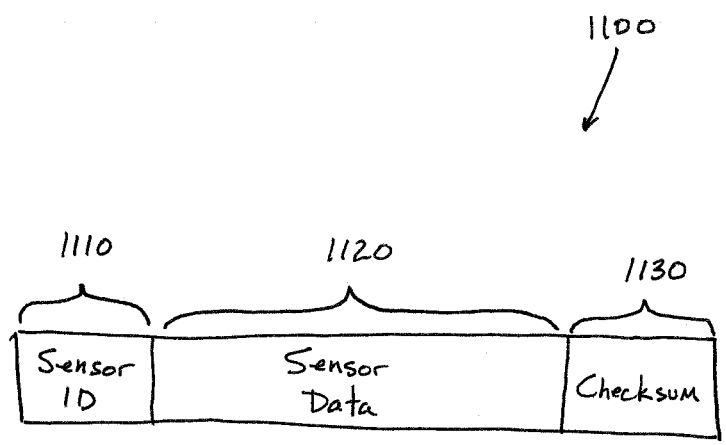
FIG. 11 an exemplary data packet transmitted by a wireless sensor.

FIG. 11 illustrates the structure of an exemplary data packet 1100 according to an embodiment. Data packet 1100 is generally constructed by processor 910 prior to transmission to wireless receiver 950. Data packet 1100 includes a sensor identifier field 1110 which may include one or more bytes uniquely identifying a mechanical sensor 160. Sensor data field 1120 may include data identifying the direction and magnitude of sensed parameters, such as acceleration, experienced by mechanical sensor 160. For example, sensor data field 1120 may indicate the magnitude of acceleration along each of three axes. A checksum field 1130 may be provided as an error correction measure. Wireless receiver 950 may use the checksum field to determine whether a transmission has been received in its entirety.

During use, the system may determine that a nerve is proximate to the stimulator by evaluating the output from the one or more mechanical sensors 160. In an embodiment, the system may make such a determination by comparing the raw output from the mechanical sensor 160 to a threshold that indicates an acceptable muscle response. Alternatively, the system may first filter the raw sensor output to eliminate high or low frequency noise prior to comparing the raw output to the threshold. In an embodiment, the system may derive additional information from the raw sensor output, and use such derived information to aid in determining nerve proximity. Such signal-derived information may include, for example, time derivatives, integrals, harmonic frequencies, response lag, or other signal-based information.

Figure 12:
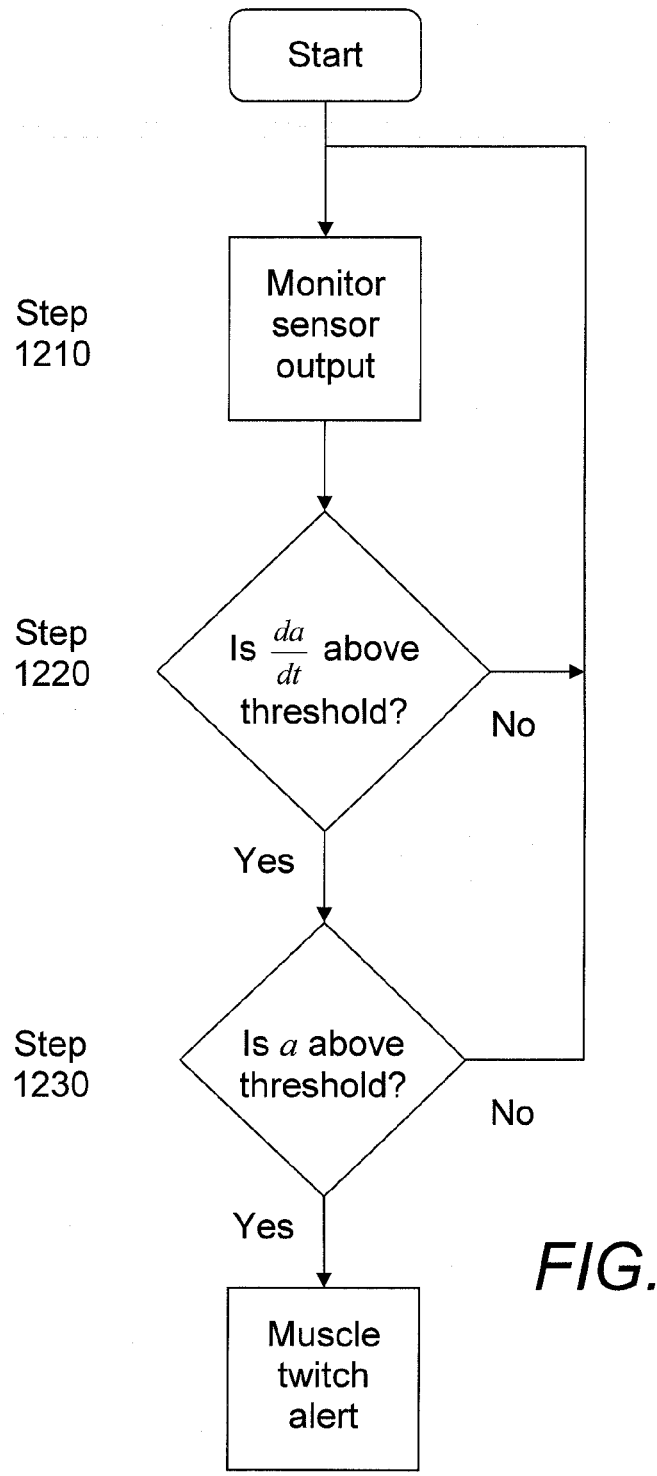
FIG. 12 is a flow chart illustrating an exemplary muscle response detection scheme.

In an exemplary embodiment, mechanical sensor 160 may comprise an accelerometer. As illustrated in FIG. 12, the system may first register raw readings from the accelerometer in step 1210. The system may then use these raw readings to derive the amount of muscle "jerk" experienced by the patient ("jerk," or a "jerk value," is the rate of change of the sensed acceleration (i.e. da/dt)). While a jerk value may be derived by taking the time derivative of acceleration, it may also be computed from other sensed mechanical parameters, such as velocity or position. It has been found that a muscle response induced by a provided stimulus may correspond to a particular jerk rate. By setting an appropriate threshold and comparing the derived jerk to the threshold (step 1220), the system may be able to initially filter recorded readings to discriminate between a stimulator induced response, a patient-intended muscle movement, and an unintended environmental response (e.g. bumping the patient table). Finally, by comparing the amplitude of the sensed acceleration to a threshold (step 1230), the system may determine whether the innervated nerve is sufficiently close to the stimulator to alert the physician. In an embodiment incorporating electrical stimulation, the system may further detect whether electrical stimulation was being transmitted during a sensed response. Doing so may allow the system to further correlate the physician's actions to the sensed response. The system may use this evaluation to alert the physician to a manual stimulus (e.g. physical contact with the nerve) if a muscle response was detected in the absence of an electrical stimulus. It should also be understood that the jerk evaluation (step 1220) may occur either before or after testing the amplitude of the sensed acceleration (step 1230) without affecting the spirit of the invention. In other embodiments, other sensed or derived parameters may be used for the purpose of identifying stimulator-induced muscle response, as well as for testing the magnitude of the induced response.

In an embodiment, the above described system may be used to aid a physician in avoiding contact with a nerve. As described above, this may be accomplished by alerting the physician when he/she brings the stimulator within a certain proximity of a nerve. In another embodiment, the above described system may be used to aid a physician in locating a particular nerve, such as during a pain management procedure. As known in the art, certain pain management procedures require injecting a local anesthetic at, or in proximity of, a sensory nerve. By locating the motor nerve through the proximity detection methods described above, the physician may more accurately identify an injection site for the anesthetic.

Figure 13:
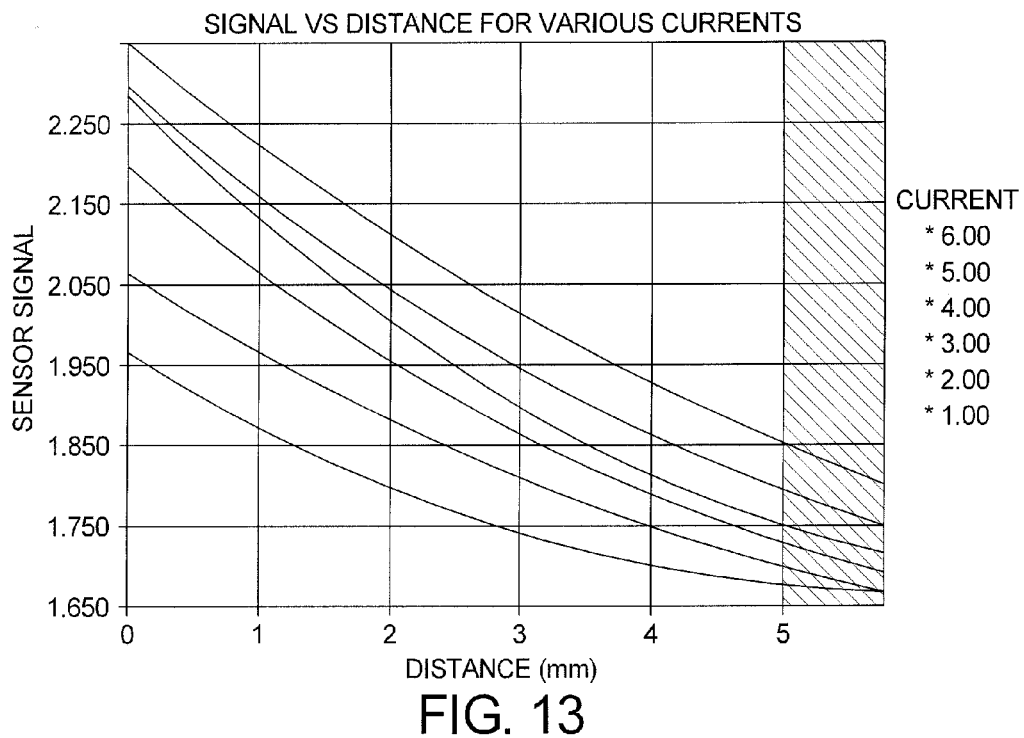
FIG. 13 is a graph illustrating an exemplary correlation between stimulator current, measured muscle response, and stimulator proximity to a nerve.

To further aid in neural proximity detection the system may be configured to determine the distance of the nerve from the stimulator based on the electrical current of the stimulus and the measured mechanical sensor signal output. As generally shown in FIG. 13, correlation graphs may be used to provide the system or physician with an idea of the magnitude of the stimulator proximity to the nerve. Correlation graphs, such as those shown in FIG. 13, may be empirically determined on a patient-by-patient basis, or may be theoretically derived based on factors such as the thickness and density of the patient's skin, subcutaneous fat, and muscle. Alternatively, general correlation graphs may be generated, and provided with confidence bands or modified to suit a particular patient based on factors specific to the patient (e.g. body mass index).

In an exemplary approach, a physician may dictate the current level that is being applied to the stimulator, if the stimulator is close enough to a nerve to induce a muscle response, the muscle sensor would generate an output signal that may be measured and quantified by the system. Knowledge of the two variables may then allow the system to determine an approximate absolute distance between the stimulator and the nerve In an embodiment, the system may have a pre-set initial current level that is selected based on the intended procedure. For example, when the software starts up the physician may be presented with a screen that inquiring as to either the type of surgical procedure being performed, or the distance away from the nerve the physician wishes to remain. The system may then use this information to adjust the threshold based on optimal current setting for the procedure or distance. The physician may also maintain the ability to vary the current level during the procedure.

Figure 14:
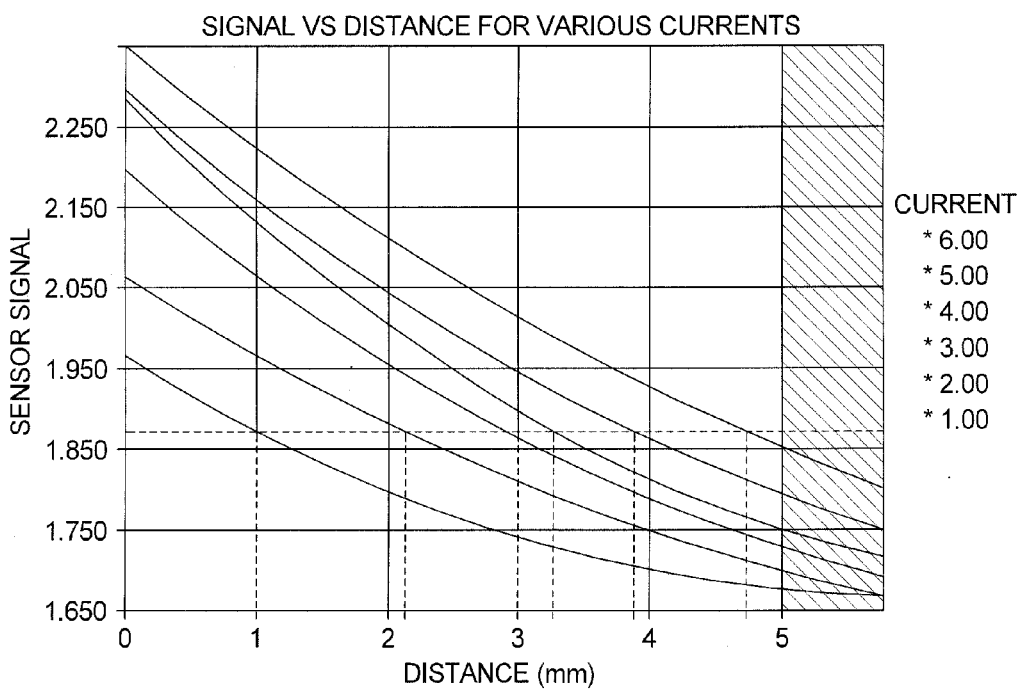
FIG. 14 is a graph illustrating an exemplary correlation between stimulator current, measured muscle response, and stimulator proximity to a nerve, along with an desired threshold.

As generally shown in the correlation graphs of FIG. 14, a threshold may be set within the range of expected sensor signal levels (e.g. as described in connection with FIG. 12 (step 1230)). Once a particular sensor signal threshold is set, a physician may then select a static current based on his/her level of confidence with the procedure. For example, as described with reference to FIG. 14, if the physician only wishes to only be alerted when he/she is within 3 mm of a nerve, given the pre-set threshold of approximately 1.86 units, the physician would conduct the procedure with a 3 mA stimulus current. Alternatively, if the physician only desired to be alerted when within 1 mm of a nerve, he/she would conduct the procedure with a 1 mA current.

Figure 15A:
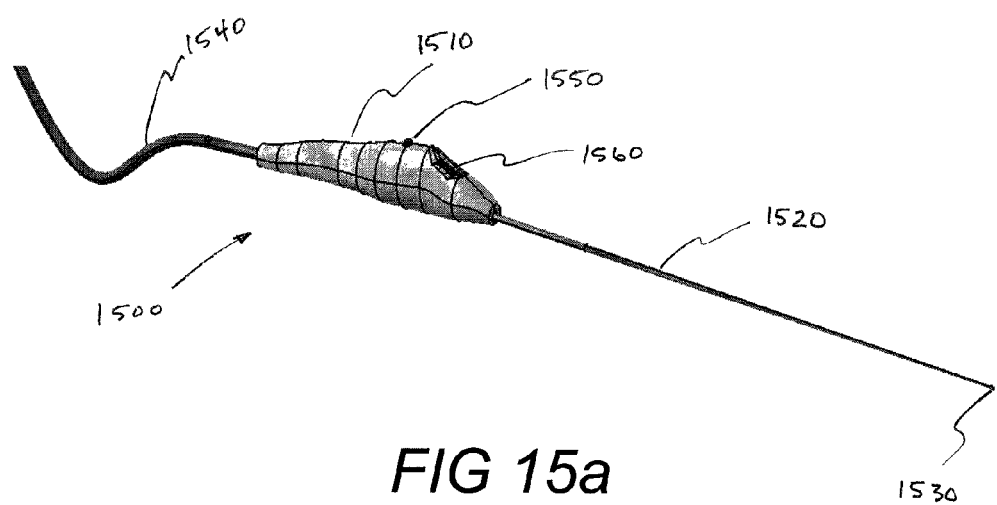
FIGS. 15a, 15b illustrate an exemplary embodiment of a stimulator probe.
Figure 15B:
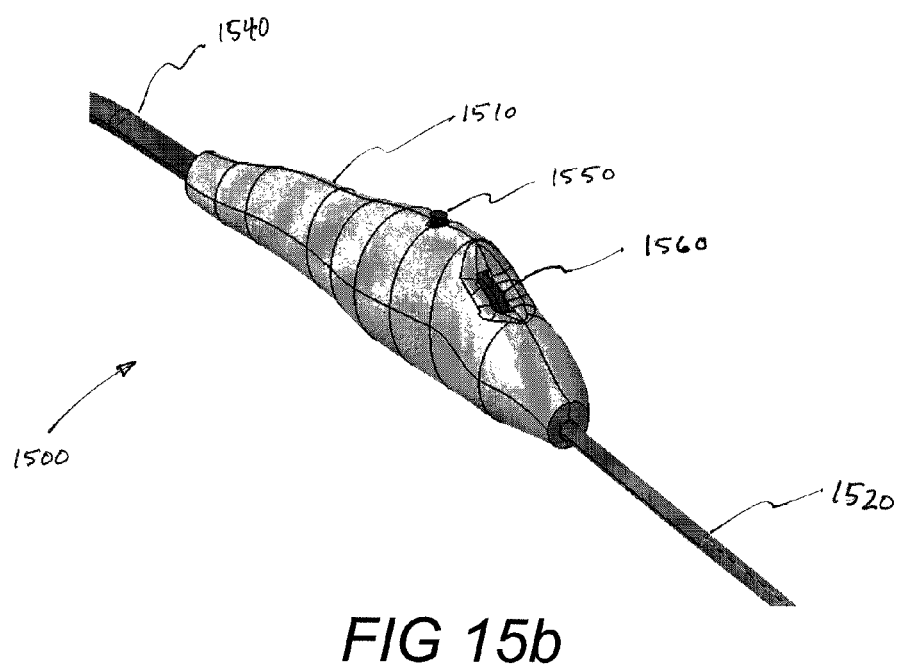

FIGS. 15*a* and 15*b* generally illustrate an embodiment of a stimulator 1500, which is similar in function to stimulator 310. Stimulator 1500 includes a handle 1510, and a stimulator probe 1520. In an embodiment, the stimulator probe 1520 may be detachable from the stimulator handle 1510, and may be replaceable with one or more different types of probes. In an embodiment, stimulator probe 1520 includes an electrode 1530 positioned at the distal end of the probe.

Handle 1510 may be connected to an electrical cable 1540 for transmitting signals to and from the stimulator 1500. Handle 1510 may include one or more buttons 1550, selector devices, wheels 1560, or LEDs. In an embodiment, a button, such as button 1550, may be configured to selectively transmit an electrical stimulus through stimulator probe 1520. In an embodiment, rotation of wheel 1560 may be configured to cycle through options on a display associated with the system, and the depression of wheel 1560 may be configured to select an option on such a display. In an embodiment, rotation of wheel 1560 may be configured to selectively vary the current intensity of the stimulus transmitted through probe 1520 and electrode 1530. Additionally, visual indicators, such as LEDs may be incorporated into handle to convey information to the physician, such as, for example, detection of a muscle response or proximate nerve, a GO/NO-GO indicator, or may simply provide feedback to the physician that the stimulator is transmitting an electrical stimulus.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A neural monitoring device, comprising:
   a stimulator configured to provide a stimulus within an intracorporeal treatment area of a subject;
   a non-invasive mechanical sensor configured to:
   be placed in contact with an external skin surface of the subject and in direct mechanical communication with a muscle of the subject; and
   generate an output signal corresponding to a sensed mechanical response of the muscle; and a processor configured to
receive the output signal from the mechanical sensor;
provide a first indicator if the sensed mechanical response is attributable to a depolarization of a nerve that is caused by the provided stimulus; and
provide a second indicator if the sensed mechanical response is not attributable to the provided stimulus.

2. The neural monitoring device of claim 1, wherein the first indicator is indicative of the nerve being proximate to the stimulator, and wherein the second indicator is indicative of a condition where it is safe to proceed with a surgical procedure.

3. The neural monitoring device of claim 1, wherein the stimulus is an electrical stimulus having a constant current.

4. The neural monitoring device of claim 1, wherein the stimulator includes a button, and wherein the stimulator is configured to selectively provide the stimulus upon actuation of the button.

5. The neural monitoring device of claim 1, wherein the processor is in communication with the stimulator; and wherein the processor is configured to selectively vary the magnitude of the stimulus.

6. The neural monitoring device of claim 1, wherein the mechanical sensor includes a contact detection device configured to detect whether the mechanical sensor is in mechanical communication with the subject.

7. The neural monitoring device of claim 6, wherein the contact detection device is configured to selectively enable the mechanical sensor when contact is detected.

8. The neural monitoring device of claim 7, wherein selectively enabling the mechanical sensor includes providing power to the mechanical sensor.

9. The neural monitoring device of claim 6, wherein the contact detection device is configured to provide an indication to the processor of detected contact between the mechanical sensor and the subject.

10. The neural monitoring device of claim 9, wherein the processor is configured to provide an alert if the mechanical sensor is not in mechanical communication with the patient.

11. The neural monitoring device of claim 1, wherein the mechanical sensor is configured to wirelessly communicate with the processor.

12. The neural monitoring device of claim 1, wherein the mechanical sensor includes an accelerometer, and wherein the output signal of the mechanical sensor corresponds to a sensed acceleration.

13. The neural monitoring device of claim 6, wherein the contact detection device is configured to monitor an electrical parameter of the subject.

14. The neural monitoring device of claim 1, wherein the processor is further configured to:
derive a time derivative of acceleration from the output signal of the mechanical sensor;
compare the derived time derivative of acceleration to a first threshold; and
determine that the sensed mechanical response is attributable to an induced depolarization of a nerve, caused by the provided stimulus, if the time derivative of acceleration exceeds the first threshold.

15. The neural monitoring device of claim 14, wherein the processor is further configured to:
compare the magnitude of the output signal to a second threshold; and
provide an alert if the time derivative of acceleration exceeds the first threshold and the magnitude of the output signal exceeds the second threshold.

16. The neural monitoring device of claim 1, wherein the processor is further configured to:
receive an indication of the magnitude of the stimulus provided by the stimulator; and
determine a distance between the stimulator and the nerve innervating the muscle of the subject from the magnitude of the stimulus and the magnitude of the output signal from the mechanical sensor; and
provide an indication of the determined distance.

17. The neural monitoring device of claim 1, wherein the stimulator includes an elongate probe having a distal end portion and wherein the stimulus is provided from the distal portion of the probe.

18. The neural monitoring device of claim 17, wherein the distal end portion of the elongate probe is movable within the intracorporeal treatment area; and
wherein the processor is further configured to provide an indicator corresponding to the position of the stimulator within the intracorporeal treatment area relative to the nerve innervating the muscle of the subject.

19. The neural monitoring device of claim 1, wherein the stimulator includes a handle and an elongate stimulator probe, and wherein the elongate stimulator probe is selectively detachable from the handle.

20. A method, comprising:
providing an electrical stimulus to a distal end portion of an elongate stimulator;
monitoring a muscle for a mechanical response to the electrical stimulus using a non-invasive mechanical sensor configured to be placed in contact with an external skin surface of a subject;
generating an output signal from the mechanical sensor, the output signal corresponding to the monitored mechanical response; and
determining, via a processor in communication with the non-invasive mechanical sensor, if the output signal from the mechanical sensor corresponds to a depolarization of a nerve in response to the stimulus provided by the stimulator;
providing a first indication to a user, via a display associated with the processor, if it is determined that the output signal from the mechanical sensor corresponds to the depolarization of the nerve in response to the stimulus provided by the stimulator;
providing a second indication to the user, via the display, if it is determined that the output signal from the mechanical sensor does not correspond to the depolarization of the nerve in response to the stimulus provided by the stimulator; and
wherein the first indication is representative that the distal end portion of the elongate stimulator is proximate to the nerve, and wherein the second indication is representative that it is safe to proceed with a medical procedure.

21. The method of claim 20, wherein the mechanical sensor includes an accelerometer; and
wherein monitoring a muscle for a mechanical response to the electrical stimulus includes monitoring an acceleration of the muscle.

22. The method of claim 20, wherein determining if the output signal from the mechanical sensor corresponds to the stimulus provided by the stimulator includes:
deriving an amount of muscle jerk from the output signal of the mechanical sensor;
comparing the derived amount of muscle jerk to a first threshold.

23. The method of claim 22, further comprising:
comparing the magnitude of the output signal to a second threshold; and
providing an alert if the amount of muscle jerk exceeds the first threshold and the magnitude of the output signal exceeds the second threshold.

24. The method of claim 20, further comprising: determining, via the processor, a distance between the stimulator and the nerve from the magnitude of the provided stimulus and the magnitude of the output signal from the mechanical sensor.

25. The method of claim 20, further comprising providing the electrical stimulus to an intracorporeal treatment area of a subject, the intracorporeal treatment area including at least one nerve innervating the at least one muscle; and
determining the position of the stimulator within the intracorporeal treatment area relative to the at least one nerve.

26. The method of claim 20, further comprising receiving an input via a button disposed on the handle of the stimulator; and
wherein providing the electrical stimulus occurs in response to the received input.

\* \* \* \* \*